(12) United States Patent
Hammer et al.

(10) Patent No.: US 11,969,345 B2
(45) Date of Patent: Apr. 30, 2024

(54) REPAIR DEVICE FOR HEART VALVE REPAIR

(71) Applicant: Children's Medical Center Corporation, Boston, MA (US)

(72) Inventors: Peter E. Hammer, Needham, MA (US); David Hoganson, Brookline, MA (US); Mossab Y. Saeed, Revere, MA (US); Pedro J. Del Nido, Lexington, MA (US); Christopher W. Baird, Boston, MA (US); Sitaram M. Emani, Newton, MA (US)

(73) Assignee: Children's Medical Center Corporation, Boston, MA (US)

( * ) Notice: Subject to any disclaimer, the term of this patent is extended or adjusted under 35 U.S.C. 154(b) by 298 days.

(21) Appl. No.: 17/258,919

(22) PCT Filed: Jul. 11, 2019

(86) PCT No.: PCT/US2019/041491
§ 371 (c)(1),
(2) Date: Jan. 8, 2021

(87) PCT Pub. No.: WO2020/014544
PCT Pub. Date: Jan. 16, 2020

(65) Prior Publication Data
US 2021/0322170 A1    Oct. 21, 2021

Related U.S. Application Data

(60) Provisional application No. 62/696,617, filed on Jul. 11, 2018.

(51) Int. Cl.
*A61F 2/24*    (2006.01)

(52) U.S. Cl.
CPC .......... *A61F 2/2457* (2013.01); *A61F 2/2463* (2013.01); *A61F 2220/0016* (2013.01); *A61F 2220/0075* (2013.01)

(58) Field of Classification Search
CPC ........................... A61F 2/2457; A61F 2/2463
See application file for complete search history.

(56) References Cited

U.S. PATENT DOCUMENTS

2004/0143323 A1*  7/2004  Chawla ................. A61F 2/2457
                                                              623/2.12
2005/0197696 A1    9/2005  Duran
(Continued)

OTHER PUBLICATIONS

Gillinov et al., "Premeasured chordal loops for mitral valve repair," The Annals of Thoracic Surgery, Sep. 1, 2016, 102(3):e269-71.
(Continued)

*Primary Examiner* — Suba Ganesan
(74) *Attorney, Agent, or Firm* — Fish & Richardson P.C.

(57) ABSTRACT

A repair device for closing a valve of a heart includes a main stem. The mains stem has a distal end and a proximal end. The main stem comprises a papillary anchor on the proximal end. The papillary anchor of the main stem is configured to attach to a papillary muscle of the heart. The main stem further includes a first branch extending from the main stem in a first direction and configured to attach to a first leaflet of the valve of the heart. The main stem also includes a second branch extending from the main stem in a second direction different from the first direction and configured to attach to a second leaflet of the valve. The first and second branches are flexible.

27 Claims, 22 Drawing Sheets

(56) References Cited

U.S. PATENT DOCUMENTS

| | | |
|---|---|---|
| 2007/0255397 A1 | 11/2007 | Ryan et al. |
| 2008/0228272 A1 | 9/2008 | Moaddeb et al. |
| 2011/0288635 A1* | 11/2011 | Miller .................. A61F 2/2457 |
| | | 606/228 |
| 2015/0094800 A1 | 4/2015 | Chawla |
| 2018/0289483 A1* | 10/2018 | Speziali ................ A61F 2/2463 |

OTHER PUBLICATIONS

PCT International Preliminary Report on Patentability in International Appln. No. PCT/US2019/041491, dated Jan. 12, 2021, 7 pages.
PCT International Search Report and Written Opinion in International Appln. No. PCT/US2019/041491, dated Sep. 26, 2019, 17 pages.

* cited by examiner

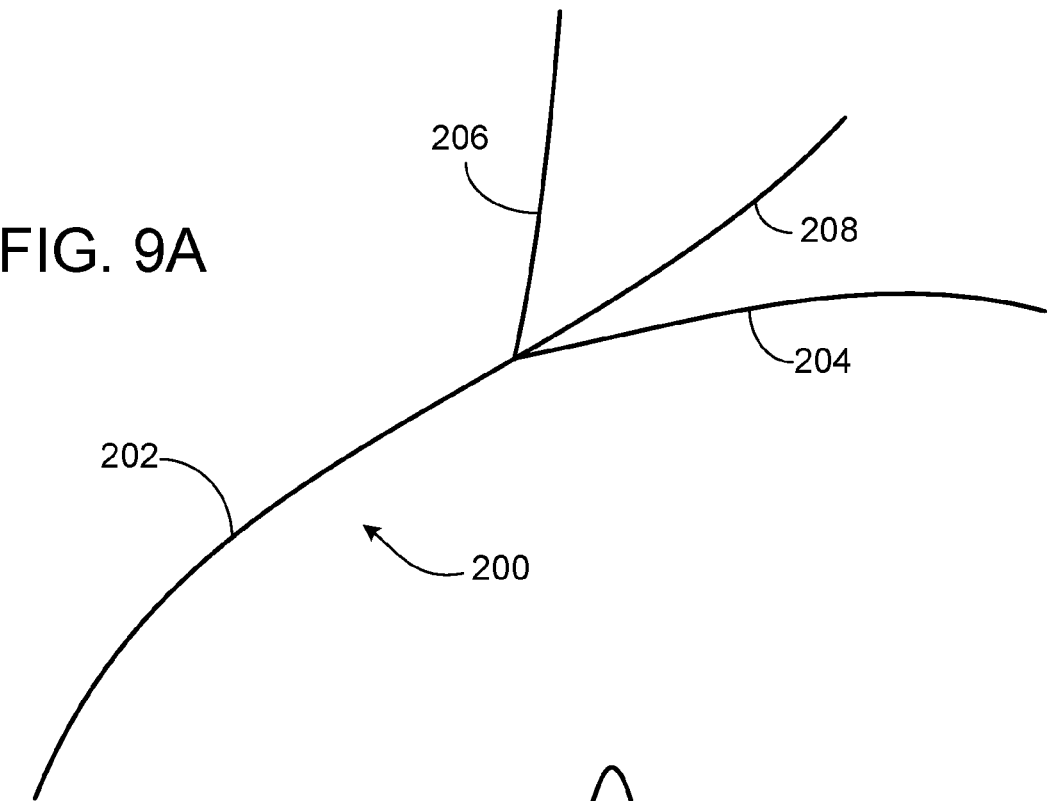
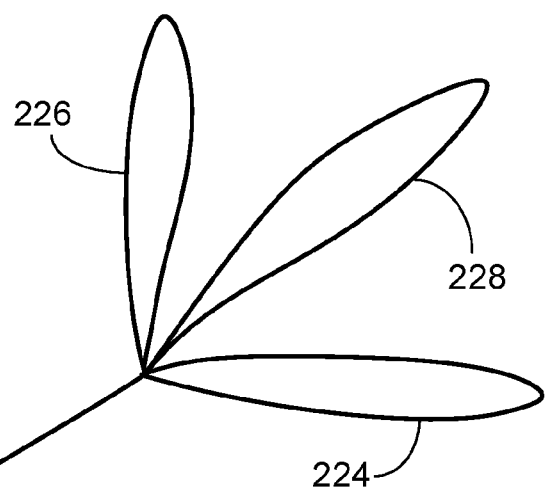

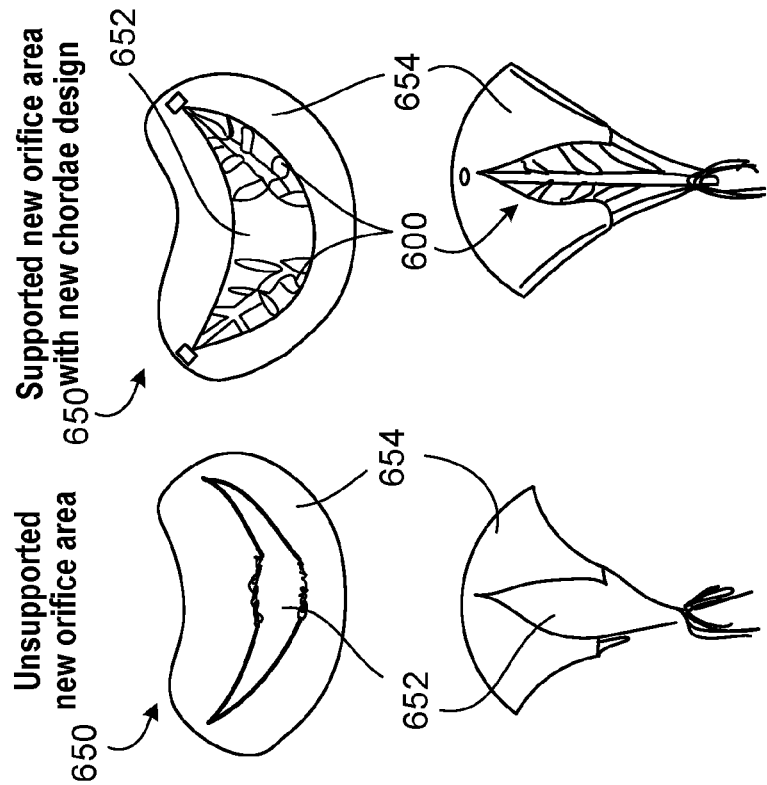
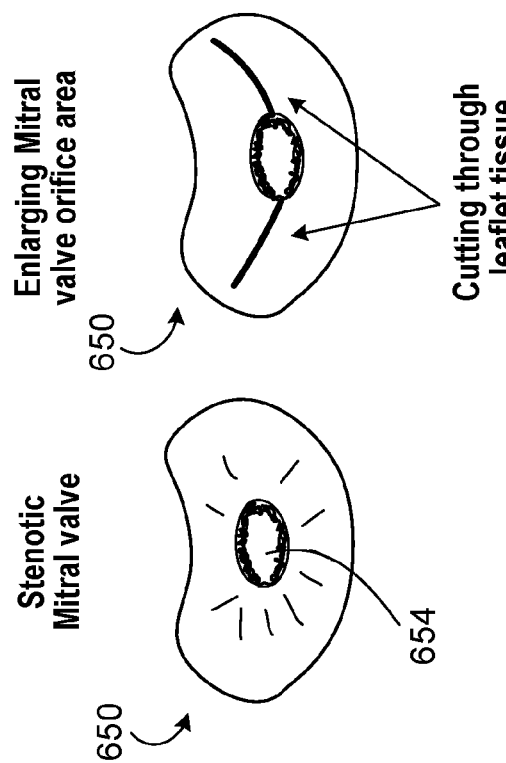
FIG. 17A  FIG. 17B  FIG. 17C  FIG. 17D

REPAIR DEVICE FOR HEART VALVE REPAIR

CLAIM OF PRIORITY

This application is a 371 U.S. National Stage Application of PCT/US2019/041491, filed on Jul. 11, 2019, which claims priority to U.S. Patent Application Ser. No. 62/696,617, filed on Jul. 11, 2018, the entire contents of which are incorporated here by reference.

BACKGROUND

The heart has two primary pumping chambers, the left and right ventricles respectively, that supply the systemic and pulmonary circulations, respectively. The inlet valves to the left and right ventricles are referred to as the mitral and tricuspid valves, respectively. The inlet valves include multiple leaflets of thin membrane that originate from the orifice that forms the ventricle input. The leaflets are opened and closed passively by changing pressure gradients created by the cyclic contraction of the heartbeat in order to create unidirectional flow throughout the circulation. The free edges of the leaflets of both valves are tethered by tendon-like structures referred to as chordae tendineae (chordae or chords) to a small number (typically 2 for the mitral and 3 for the tricuspid) of muscular outcroppings (papillary muscles) on the wall of ventricle below. These chords support the edges of the leaflets much like the lines that support a parachute. In the normal mitral and tricuspid valve, the chords are numerous and their arrangement is complex, including an arrangement of well over 100 segments including many that branch in irregular patterns. For both valves, the chords are critical to valve function, and rupture or elongation of even a single chord can cause the valve to leak. Valve leak (regurgitation), if significant, can overwork the heart and result in heart failure and, ultimately, death.

SUMMARY

This disclosure relates to the repair of heart valves by implanting a repair device including support chords. The support chords are attached to heart valve tissue, e.g., during surgery or another interventional procedure. The repair device, when surgically implanted e.g., in a mitral or tricuspid valve cleft or commissure, develops tension in the branches (also referred to as arms or chords) of the device during valve closure to directly pull the edges of the cleft or commissure together. The repair device includes a main stem that is anchored at a papillary muscle of the heart. Multiple branches, e.g., pairs of branches, emanating from the main stem are attached to opposite sides of the cleft or commissure and form a large included angle when the valve is open so that a large component of the tension in the branches acts to pull the cleft or commissure closed.

In some patients, there exists a cleft or opening in the anterior leaflet of the mitral valve or in other parts of the mitral and tricuspid valves. One example of this is complete or partial canal defects. In other complex cases, there is mixed valvar disease with a combination of regurgitation and stenosis. The repair device can support mitral and tricuspid valve leaflets while allowing substantial inflow and avoiding stenosis while treating the regurgitation.

In an aspect, a repair device for repairing a valve of a heart includes a main stem having a distal end and a proximal end, a papillary anchor disposed on the proximal end of the main stem, wherein the papillary anchor is configured to attach to a papillary muscle of the heart, a first branch extending from the main stem in a first direction and configured to attach to a first leaflet of the valve of the heart, and a second branch extending from the main stem in a second direction different from the first direction and configured to attach to a second leaflet of the valve. The first and second branches are flexible.

Embodiments can include one or more of the following features.

The repair device includes an annulus anchor disposed on the distal end of the main stem, wherein the annulus anchor is configured to attach to a wall of the heart.

When the papillary muscle is relaxed, the device is configured to be in a relaxed configuration in which the first and second branches are untensioned.

When the papillary muscle is contracted, the device is configured to be in a flexed position in which the first and second branches are taut. The main stem is configured to move away from the first and second leaflets when the repair device moves from a relaxed position to the flexed position.

The main stem extends along a longitudinal axis and the first and second branches extend from the main stem at an angle relative to the longitudinal axis.

The main stem is a ribbon.

The main stem has a circular or rectangular cross section.

The device comprises a plurality of first and second branches.

The first branch comprises multiple sub-branches, at least one of the sub-branches extending in a direction different from a direction which at least one other of the sub-branches extends. At least one of the sub-branches extends in a direction parallel to the second direction. The second branch comprises multiple sub-branches, at least one of the sub-branches extending in a direction different from a direction which at least one other of the sub-branches extends. At least one of the sub-branches extends in a direction parallel to the first direction.

At least one of the first and second branches comprises a loop.

At least one of the main stem, the first branch, and the second branch comprises a series of adjacent loops.

The first branch connects to an edge of the first leaflet.

The second branch is configured to attach to an edge of the second leaflet.

The papillary anchor is configured to be sutured to the papillary muscle.

The second branch is configured to be attached to an underside of the second leaflet.

The first and second directions are parallel.

The main stem is made from tissue engineered material. The tissue engineered material is configured to change the length of the main stem.

The main stem is configured to be mechanically adjusted to lengthen or shorten a length of the main stem.

In an aspect, a method for closing a mitral cleft in a valve of a heart includes attaching, to a papillary muscle of the heart, a papillary anchor of a repair device; attaching a first branch of the repair device to a first leaflet of the valve of the heart; and attaching a second branch of the repair device to a second leaflet of the valve.

Embodiments include one or more of the following features.

Attaching, to a papillary muscle of the heart, a papillary anchor of a repair device comprises suturing the papillary anchor to the papillary muscle.

Attaching a first branch of the repair device to a first leaflet of the valve of the heart comprises suturing the first branch to the first leaflet.

Attaching a second branch of the repair device to a second leaflet of the valve of the heart, comprises suturing the second branch to the second leaflet.

The closure device has a first configuration and a second configuration. In the first configuration the first and second branches are relaxed. In the first configuration the papillary muscle is relaxed. In the second configuration the first and second branches are tensioned and apply a force to the first and second leaflets. The force moves the valve from an open position to a closed position. In the second configuration the papillary muscle is flexed.

The method includes lengthening or shortening the lengthening of a main stem the repair device.

BRIEF DESCRIPTION OF THE DRAWINGS

FIG. 9A-9F show examples repair devices.

FIGS. 17A-17D show a repair device in use during a surgery.

DETAILED DESCRIPTION

This disclosure relates to the repair of heart valves by implanting a repair device including support chords. The support chords are attached to heart valve tissue, e.g., during surgery or another interventional procedure. The repair device, when surgically implanted e.g., in a mitral or tricuspid valve cleft or commissure, develops tension in the branches (also referred to as arms or chords) of the device during valve closure to directly pull the edges of the cleft or commissure together. The repair device includes a main stem that is anchored at a papillary muscle of the heart. Multiple branches, e.g., pairs of branches, emanating from the main stem are attached to opposite sides of the cleft or commissure and form a large included angle when the valve is open so that a large component of the tension in the branches acts to pull the cleft or commissure closed.

Figure 1:
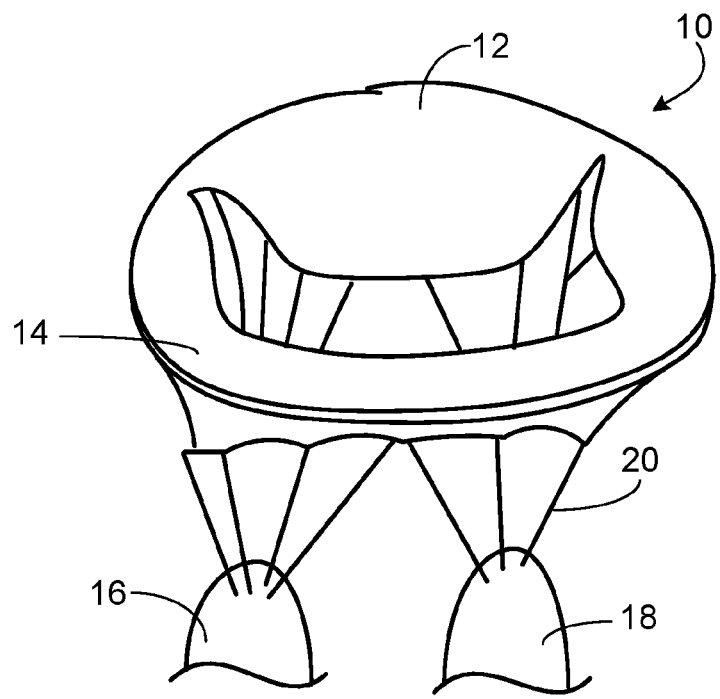
FIG. 1 shows mitral valve leaflets and a subvalvar apparatus.

Referring to FIG. 1, a mitral valve 10 is shown as viewed from the left atrium. The mitral valve 10 has an anterior leaflet 12 and a posterior leaflet 14. A subvalvar apparatus is shown below the mitral valve 10 in a cutaway view of the left ventricle. The subvalvar apparatus includes an anterior papillary muscle 16 and a posterior papillary muscle 18 as well as a supporting chords 20 which emanate from the papillary muscles 16, 18 and connect to the anterior and posterior mitral valve leaflets 12, 14. In the normal mitral valve anatomy, the chords from the posterior papillary muscle support both anterior and posterior leaflets. Likewise, chords from the anterior papillary muscle support both anterior and posterior leaflets.

Figure 2:
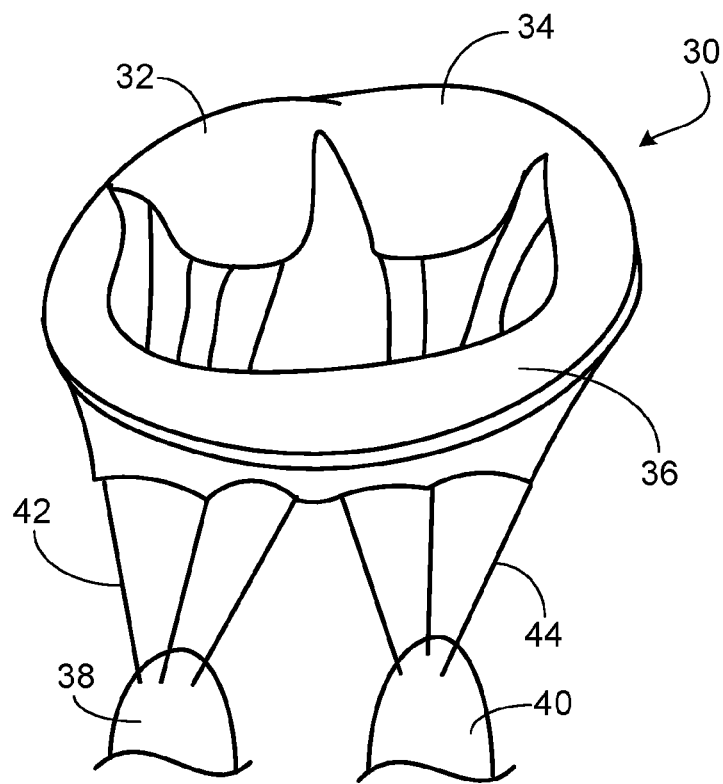
FIG. 2 shows a mitral valve with a cleft in the anterior leaflet and a subvalvar apparatus.

FIG. 2 shows a mitral valve with a cleft 30, from a view from the left atrium with a cutaway showing the sub mitral apparatus. The sub mitral apparatus includes a superior bridging leaflet 32, an inferior bridging leaflet 34, and a mural leaflet 36. The subvalvar apparatus includes the anterior papillary muscle 38, a posterior papillary muscle 40, and supporting chords 42 and 44 emanating from the papillary muscles 38, 40 to the valve leaflets 32, 34, 36.

FIG. 2 shows an example of a cleft in a mitral valve anterior leaflet, e.g., as part of a complete AV canal defect or partial AV canal defect. Clefts can also be seen in the posterior mitral valve leaflet. There are multiple cleft configurations, including additional secondary clefts that occur transversely within the superior bridging leaflet, and clefts can occur in any aspect of the tricuspid valve. A cleft is typically supported by one papillary muscle giving chords to side of the cleft and a separate papillary muscle giving chords to the other side of the cleft. There can be variations on clefts, including a deformity known as a parachute mitral valve in which a single papillary muscle has chords supporting a valve emanating from a single papillary muscle, and in which here is no secondary papillary muscle. In this configuration the anterior papillary muscle on the mitral valve is often the sole papillary muscle. Patients with a parachute mitral valve sometimes have a deficient mural leaflet 36 and thus when the cleft in the anterior leaflet is closed this results in a very small orifice for the mitral valve.

Figure 3:
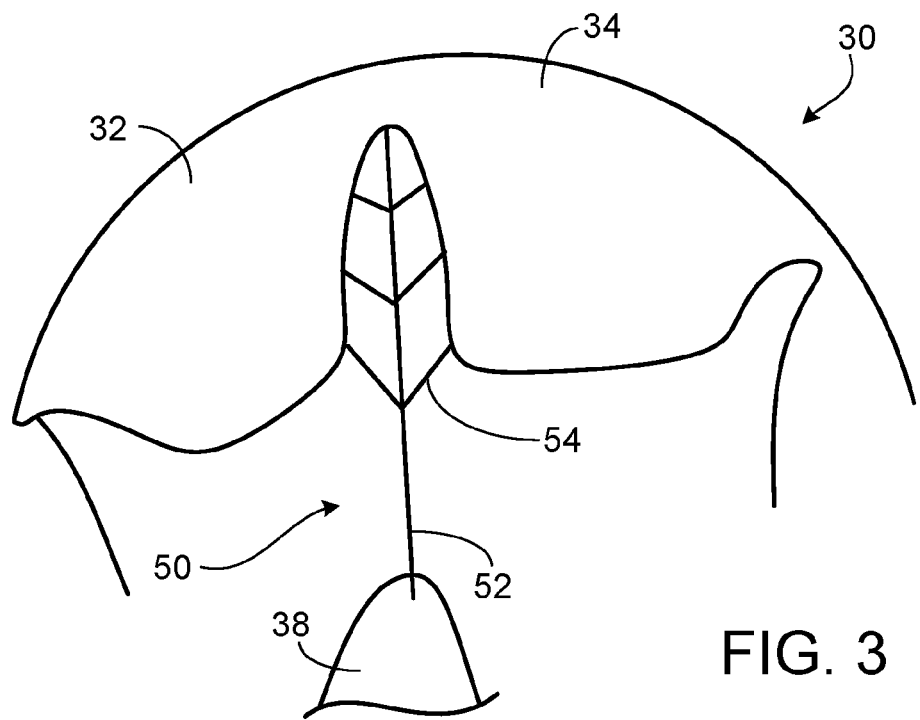
FIG. 3 shows a mitral valve with a cleft in the anterior leaflet supported by a repair device.

Referring to FIG. 3, a cleft mitral valve 30 includes a superior bridging leaflet 32 and inferior bridging leaflet 34 with anterior papillary muscle 38. A repair device 50 includes a main stem 52 which is attached at one end to the papillary muscle 38 and the other end at the annulus of the mitral valve 30. This repair device has multiple branches 54, such as pairs of branches, that extend from the main stem 52 and support the edges of the cleft between the superior bridging leaflet 32 and the inferior bridging leaflet 34. During systole as the ventricle contracts and pressurizes, the opposing pairs of branches 54 act to pull leaflet edges of the superior bridging leaflet 32 and the inferior bridging leaflet 34 together thereby closing the cleft and preventing regurgitation of blood through the cleft. The main stem 52 is anchored on the annulus at one end and the papillary muscle 38 at the other end. During ventricular contraction the papillary muscle also contracts and moves medially. This action creates tension on the main stem 52 pulling it slightly downward. The pairs of branches 54 (arms) of the repair device 50 then effectively oppose the cleft edges.

In some examples, the lengths of the main stem 52 and pairs of branches 54 can be sized to achieve a desired level of tension and leaflet apposition. The appropriate lengths of the main stem 52 and branches 54 can be determined, e.g., by echocardiographic assessment of the anatomy of the ventricle and the valve, intraoperative measurements to confirm the relative distances between attachment points of the repair device, or other approaches. For instance, imaging modalities such as MRI, computed tomography, and/or catheter-based imaging can be used to add additional information on the position of the chordal structures to inform the sizing of the branched chordae system. Three-dimensional echocardiography can also be used. Post-acquisition analysis of echocardiographic and three-dimensional echocardiographic images can be done to further obtain measurements between a first and second anchor points of the repair device.

The first and second anchor points of the repair device are at the papillary muscle 38 (papillary anchor point) and the annulus (annulus anchor point) of the anterior leaflet of the mitral valve 30. The anterior leaflet annulus can be, e.g., a ventricular septal defect (VSD) patch (e.g., in the case of a complete AV canal during repair) or the crest of the ventricular septum (e.g., in the case of a partial or transitional AV canal). The second anchor point can be below the level of the annulus on the ventricular septum. The takeoff for the chord can be within the ventricle, e.g., not necessarily on the papillary muscle. The repair device can be placed in a closure of a commissure or other cleft-like valve openings. In such applications, the second anchor point and the first anchor point of the main stem 52 could be at any appropriate position within the ventricle. In some cases, the main stem does not lie directly in line with the cleft, commissure, or opening that is being supported by the repair device. The first anchor point within the ventricle, for example on the muscle, can be in a lower position within the ventricle than the second anchor point, which can sometimes be near the annulus of the valve. In some cases, the main stem attaches at one end to the papillary muscle and the other into the mitral valve annulus at the level of the cleft, and the multiple pairs of branches 54 have different lengths. The two branches of a pair are generally the same length but may be different, and the lengths of the branch pairs can get shorter as the pairs near the mitral valve annulus.

Figure 4A:
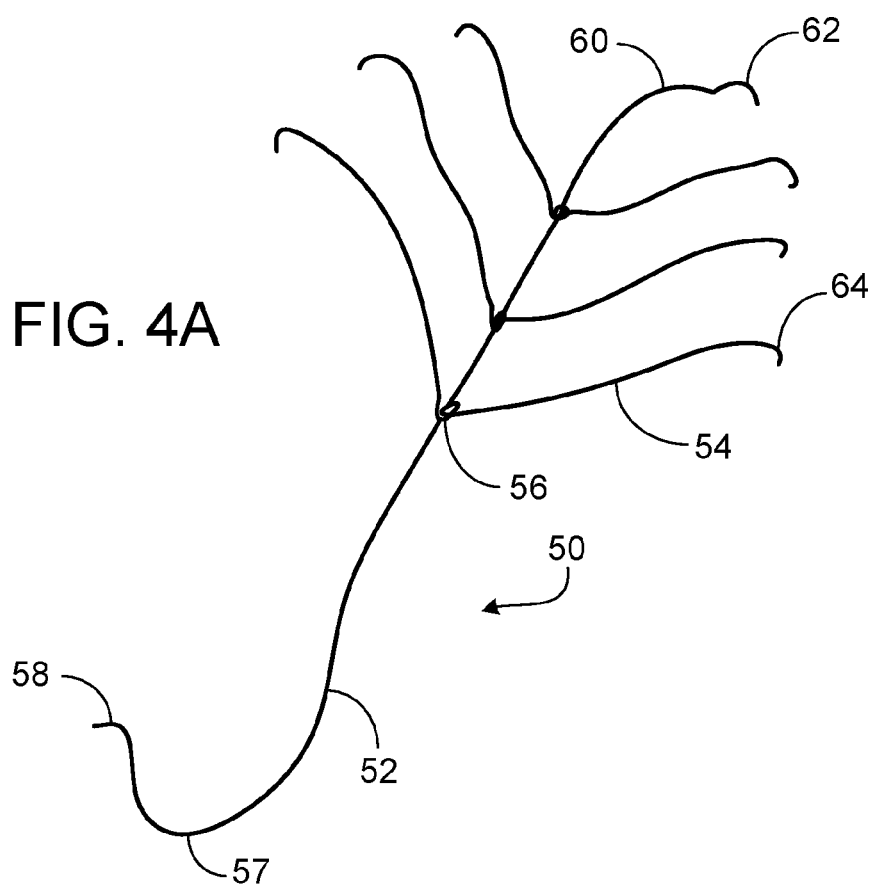
FIG. 4A shows an example repair device.

Referring to FIG. 4A, a repair device 50 includes the main stem 52 and multiple branches 54. In the example of FIG. 4A, the branches 54 come off the main stem 52 in pairs emanating from a common or near common attachment 56 to the main stem 52. The repair device 50 can be constructed in a variety of ways. For example, the branches 54 can be individual filaments attached to the main stem 52. In this configuration, each branch length is fixed relative to the main stem 52. In some examples, the pairs of =branches may slide relative to their attachment on the main stem to enable self-adjustment after implantation. The main stem 52 has a proximal end 57 and a distal end 60. In some examples, the main stem can have a needle 58 attached to the proximal end 57 whereby the proximal end can be attached to a structure, for example papillary muscle.

In some examples, the proximal end of the main stem can be passed through a pledget or other similar structure to disperse the force across a wider area of the first anchor point. In some examples, the distal end can have a needle which facilitates attachment of the main stem to the supporting structure at the second anchor point such as the annulus of the mitral valve. The length of the main stem at the proximal and distal ends prior to the needle can be elongated compared to the intended final length of the implanted main stem so that the needle can be handled and passed through the tissue and tied down. The excess main stem length past the knot on the proximal and distal ends can then be trimmed. Each of the branches 54 can have a needle 64 attached thereto which allows the distal end of the branches to be passed through the leaflet tissue of the mitral and tricuspid valve and tied down to the desired length. Similar to the main stem, the branch length can be markedly longer than the intended final implant branch length to allow needle handling and tying of the knot.

Figure 4B:
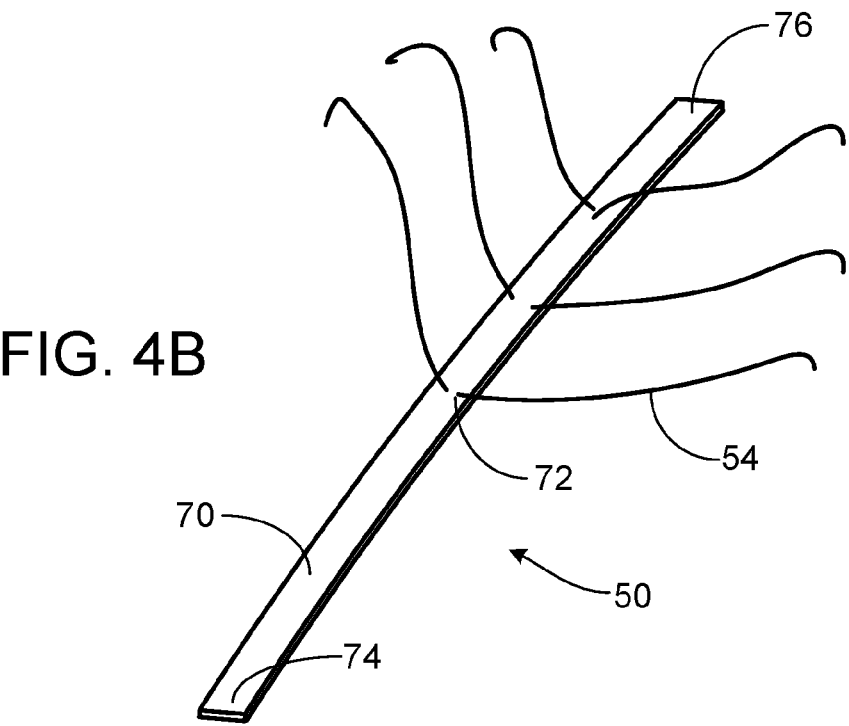
FIG. 4B shows an example repair device.

Referring to FIG. 4B, an example repair device 50 includes a main stem 70 having a ribbon-like structure. One or more branches 54 are attached to the main stem 70 at attachment points 72. The main stem 70 has a proximal end 74 and a distal end 76. The main stem 70 is fabricated of inflexible material. Some main stems are fabricated of flexible material. Flexible materials may include a strip of polytetrafluoroethylene (PTFE) or expanded PTFE material. Other examples of materials suitable for the main stem include braided or woven filaments such as sutures or other fabric such as a Dacron, polymeric materials, nonpolymeric filament materials, resorbable materials, nonresorbable materials, human or animal extracellular matrix materials (e.g., preserved or decellularized) such as chordal tissue or other ECM tissues including ligament or tendon tissues, decellularized dermis, small intestinal submucosa, mesothelium, dura, or other protein containing materials. The main stem can be a stiff material or an elastomeric material. In some examples, the material of the main stem is mechanically adjustable to enable the length of the main stem to be changed, e.g., increased. For example braided materials, elastomeric materials, and bioengineered tissues (animal extracellular matrix materials), are stretchable to elongate and lengthen the main stem. In some examples, the material of the main stem can be mechanically adjustable to decrease the length of the main stem. For example braided materials, elastomeric material, and bioengineered tissue (animal extracellular matrix materials), are condensable to shorten the main stem. The material may also be soft so that a portion of the main stem or branches can be mechanically removed using a blade or scissors.

The branches of 54 are fixed at a common point 72 on the main stem 70. In some repair devices, the pairs of branches can be continuous and attach in such a way that they can slide through the main stem 70 to balance the total length between the two branches. The branches can be constructed of synthetic material such as PTFE or other polymers typical for suture material. Filaments can also be a variety of extracellular matrix, polymeric, resorbable, or nonresorbable materials including or similar to but not limited to those described above for the main stem.

Figure 5A:
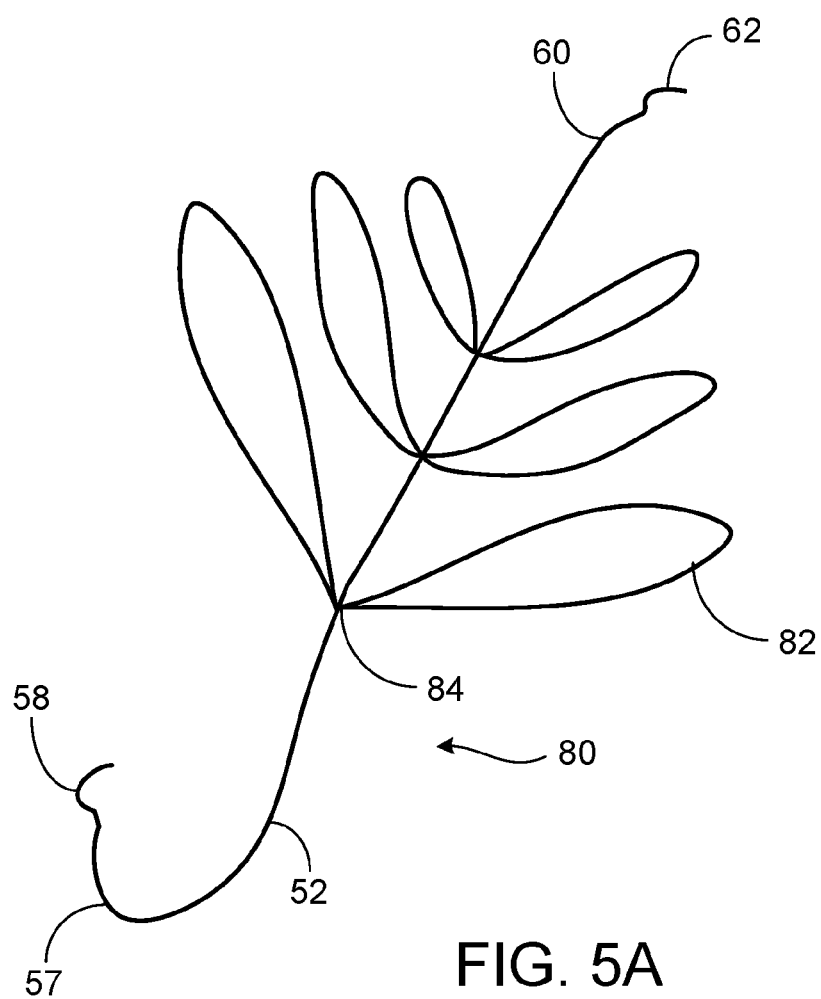
FIG. 5A shows an example repair device.

Referring to FIG. 5A, a repair device includes the main stem 52 and branches 82 in the form of loops. The repair device can include one or more branches with a loop configuration. These branches 82 can be present in pairs. Some branches can be individual loop branches that extend from the main stem. Each branch 82 is fixed to the main stem 52 at a fixation area 84 (junction) which can be the same fixation area 82 for the opposing branch 82. Some fixation areas are near the fixation area for the opposing branch. The loop branches 82 can be affixed to the main stem 52 such that the loops can slide through the main stem and distribute the length between the pair. Some loops are individually affixed to the main stem without capacity for the lengths to change. The main stem has a proximal end 57 and a distal end 60.

Some proximal end 57 and distal ends 60 have needles 58 and 62 to allow easy attachment to the supporting cardiac structures.

Figure 5B:
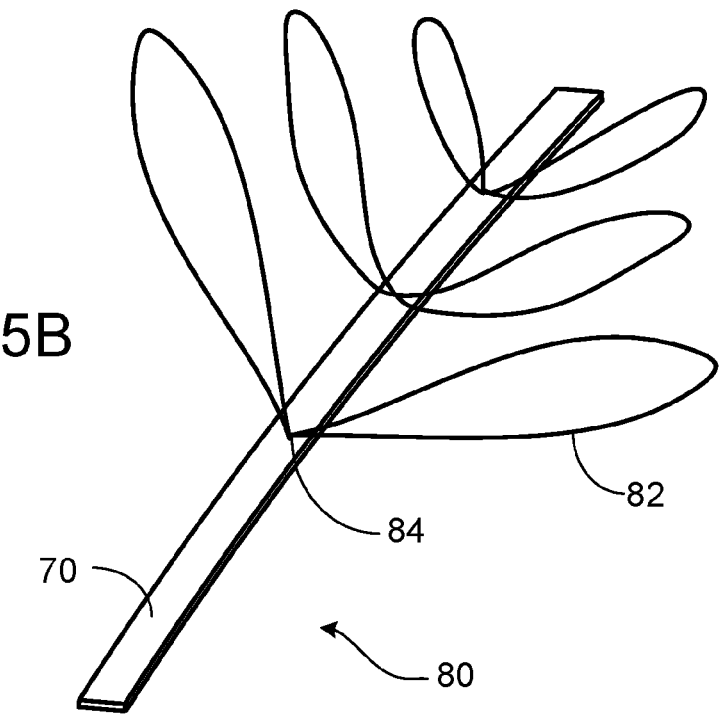
FIG. 5B shows an example repair device.

Referring to FIG. 5B, a repair device has a main stem 70 and branches 82 with proximal attachments 84. This main stem 70 is a ribbon-like structure with an aspect ratio different than 1:1. The loop branches affix to the main stem 70 as individual branches, a single branch, pairs of branches, or any complex combination of branches. The main stem 70 itself can be a linear element or could have one or more fixation areas. For example, at a first and/or second anchor point for the main stem at either end including a branched proximal end that attaches to both papillary muscles with a single distal attachment end near the valve annulus. The main stem is sized to receive sutures for anchoring the main stem to the heart structures, such as the papillary muscles and annulus.

Figure 6:
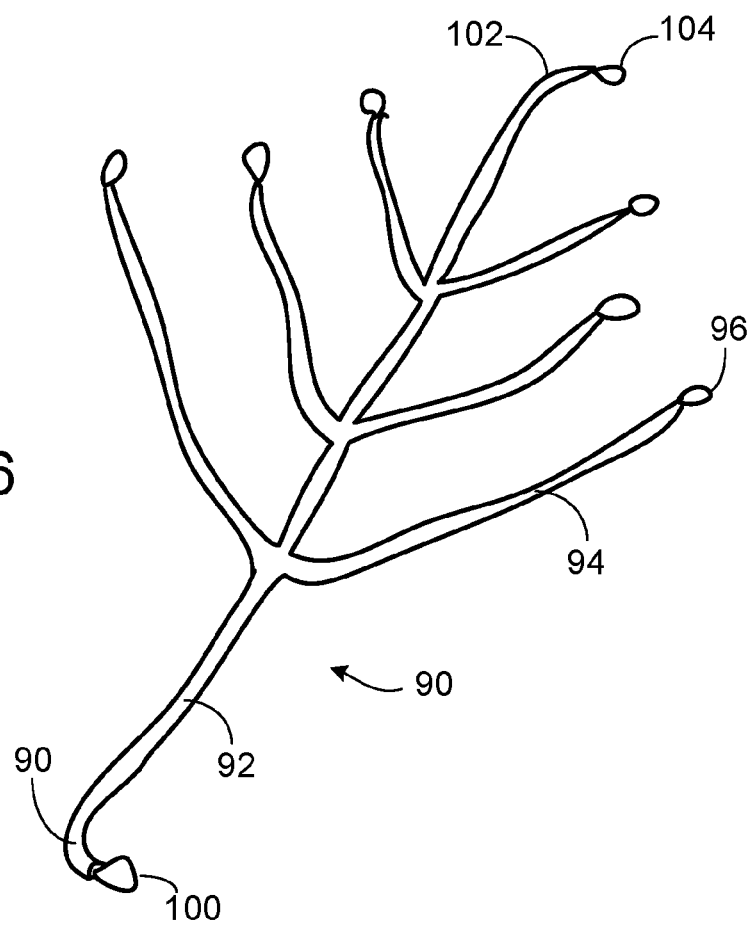
FIG. 6 shows an example repair device.

Referring to FIG. 6, a repair device 90 includes a main stem 92 having proximal end 98 with distal end 102. There are one or more branches 94 emanating from the main stem. The branches 94 and main stem 92 are a continuous structure with a cylindrical cross section. Some branches and main stems have a another shape including square, rectangular, or other uniform or non-uniform cross-sectional shape. The repair device may have loops 96 for attachment which are at the ends of one or more branches 94. Some main stems have loops at the proximal end 98 or the distal end 104 for attachment. These loops act as first and second anchors (papillary and annulus anchors) to receive sutures that attach the first and second anchors to the anchor points within the ventricle or annulus of the valve by passing suture through the loops and tying the loops down. Some sutures pass through the valve leaflets and secure the loops of the branches. In this configuration, the lengths of the branches and main stem can be set prior to implantation and allows for ease of suture retention by the surgeon without having to adjust the length of the branch during the tying of the knot to secure to the cardiac structure. The repair device is a single piece that is cast, molded, injection molded, extruded, or otherwise manufactured. Some repair devices are assembled as individual pieces, being assembled together prior to implantation to be a functionally similar device.

Figure 7:
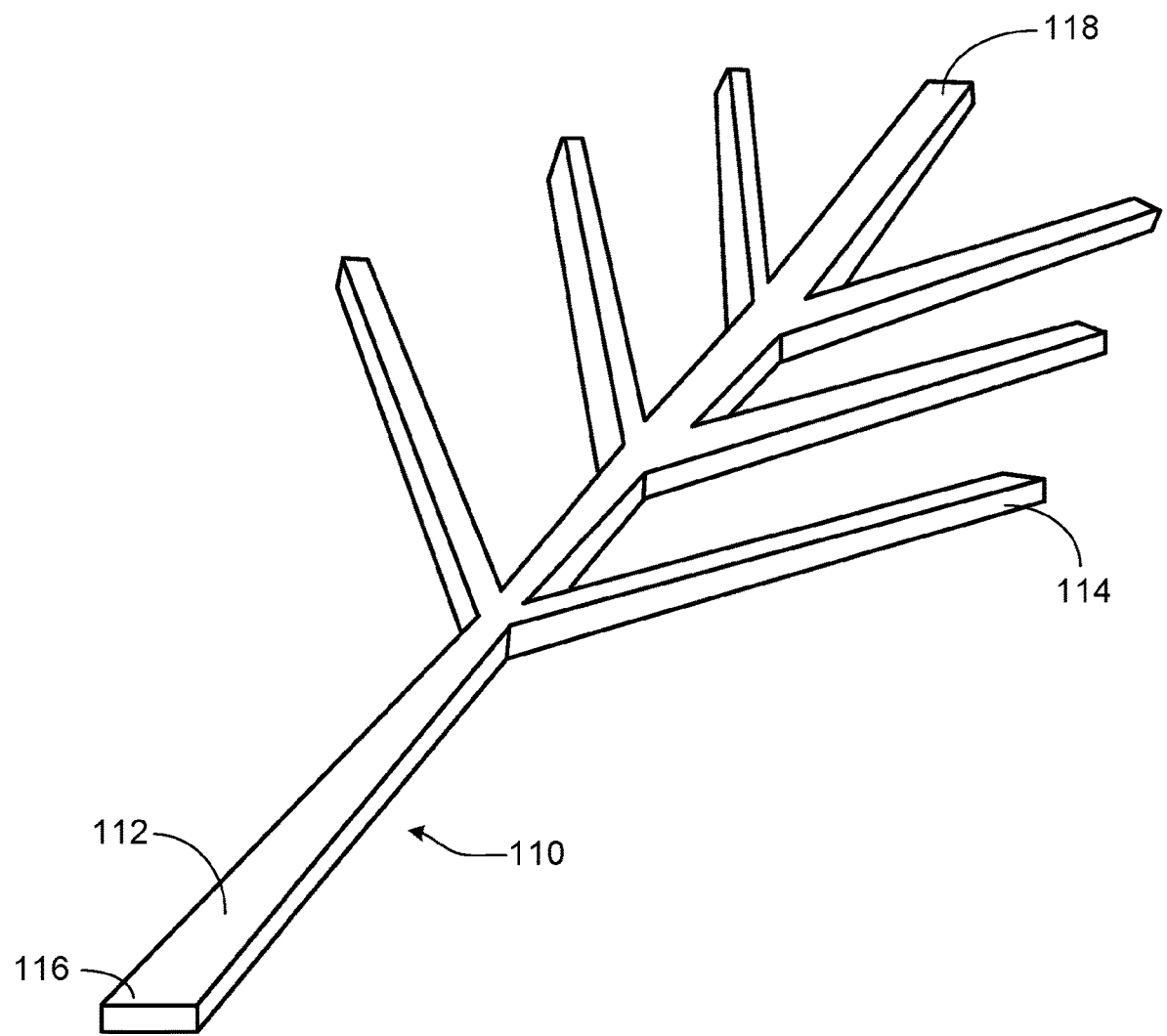
FIG. 7 shows an example repair device.

Referring to FIG. 7, a repair device 110 has a main stem 112 with proximal end 116 and distal end 118. There are one or more branches 114 that emanate from the main stem. In the example of FIG. 7, the main stem 112 and the branches 114 are each of a ribbon-like structure (membrane, or sheet) with aspect ratio that is equal to or different than 1:1. The stiffness and strength of the main stem and the branches is different, however in come repair devices, the stiffness and strength of the main stem and the branches are the same. Likewise the size of the main stem 112 or branches 114 could be similar or different.

Figure 8A:
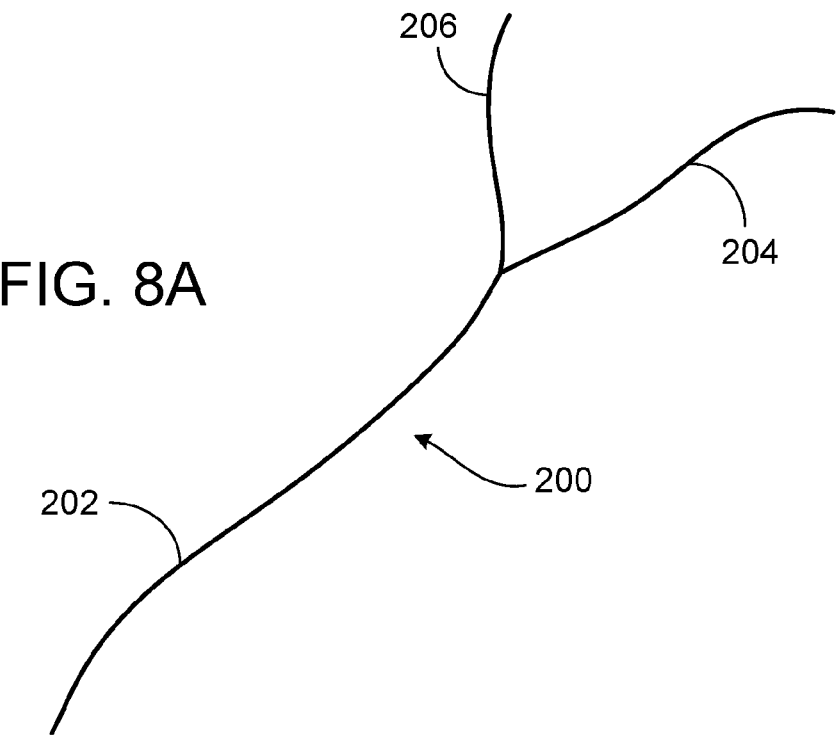
FIG. 8A shows an example repair device.

Referring to FIG. 8A, a repair device 200 includes a main stem 202 and branches 204 and 206. The main stem 202 may be anchored at one or more than one points of the ventricle. In one embodiment the main stem is only anchored at its proximal end, and the branches 26, 204 of the device 200 may each be anchored to the leaflet material. In this embodiment of the repair device, the branches may be attached to different points on a single leaflet or to two separate leaflets. The branches 204 and 206 may be of equal length or may be of different lengths. Additionally, the main stem and branches may have needles attached to them or they may be without needles. As shown in similar previous embodiments the main stem and branches may be ribbon-like, of circular cross-section, or of another cross-sectional shape as may be beneficial for their implantation and or function. In some valve disease, it is typical for the leaflets to have lost the integrity of their native chordal support. The normal mitral and tricuspid valve chordal support is a complex array of chords that can exceed 100 total chords for the entire valve. This includes edge chords, or marginal chords, that attach to the leading edge of the leaflet. It is these chords that are typically replaced in current surgery where artificial chords are utilized. The normal support of a valve includes secondary chords which attach along the underside of the valve leaflets including in the area of coaptation between valve leaflets as well as to the flat portion of the leaflet that emanates from the valve annulus. It is typical of these chords to attach in multiple places from the leading edge of the leaflet to approximate halfway between the leading edge in the annulus of the valve. The secondary or more basally positioned chords are larger in diameter and have larger collagen fiber bundles and higher stiffness suggesting they bear a tremendous amount of the load of closure of the valve leaflets. These chords are essential to form the normal shape of the mitral and tricuspid valves and in some patients it may be advantageous to implant artificial chordae supports for these secondary chords in addition to or independent of placing edge or primary or marginal chords. In the case where a valve requires support of the edge of leaflet as well secondary chords, in this embodiment, the branches 204 and 206 may be implanted on the edge of leaflet as well as in a secondary chord position. In this embodiment the lengths of the branches 204 and 206 may be different. In another embodiment, both branches 204 and 206 could be used to support the leaflet edges. In another embodiment, both branches 204 and 206 can be used to support the underside of a leaflet as secondary chords. In another embodiment, both branches 204 and 206 can be used to support a commissure or cleft.

Figure 8B:
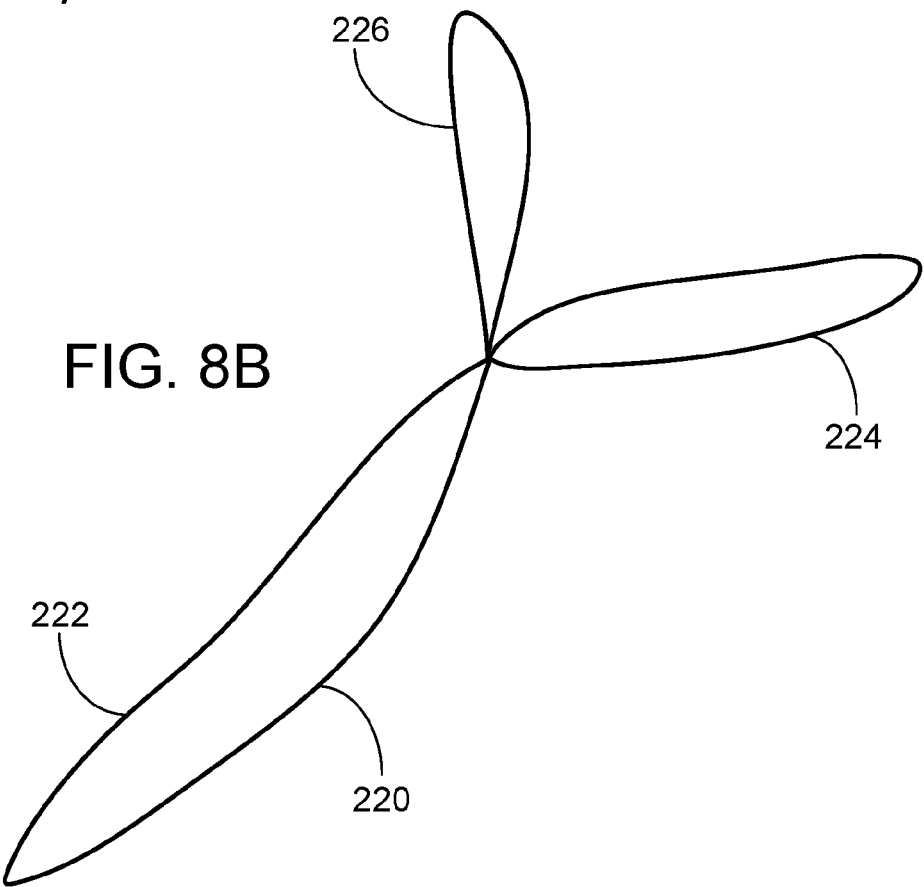
FIG. 8B shows an example repair device.

Referring to FIG. 8B, a repair device 220 includes a main stem 222 and branches to 224 to 226. The main stem 222 can be a single filament or a loop as is shown in this embodiment. Likewise the branches 224 and 226 may be loops as is shown in this embodiment, filaments, or a combination of filaments and loops. The utility of the loops is such that the length of the main stem 222 and branches 224 and 226 could be fixed length. They could then be secured to the necessary cardiac attachment points of the papillary muscle and leaflets in one embodiment. Securement through loops with suture allows the surgeon to securely tie a suture down without having to utilize the knot of the suture to adjust the length of the branches or the main stem.

Figure 8C:
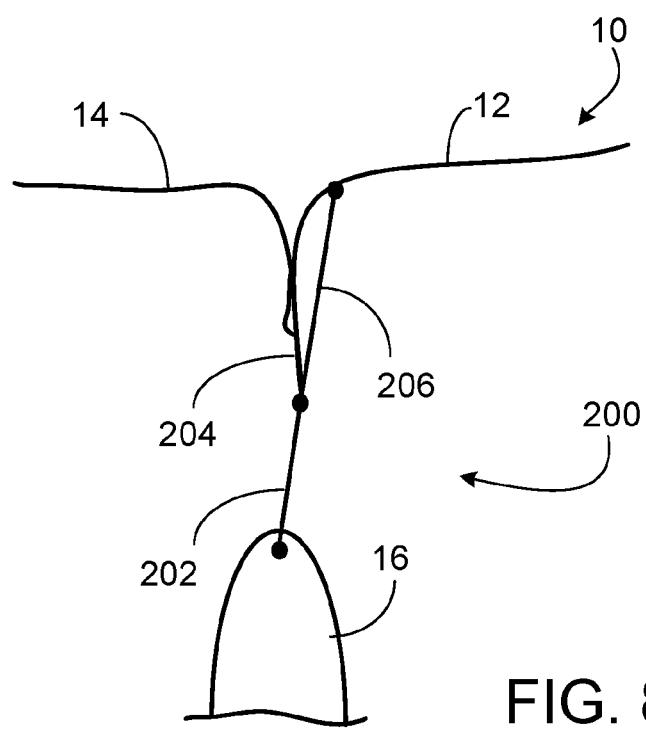
FIG. 8C shows a mitral valve with a repair device.

Referring to FIG. 8C, a mitral valve 10 is shown in a cut cross-section with anterior leaflet 12 and posterior leaflet 14 with anterior papillary muscle 16 shown in a partial cutaway view of the ventricle. There is a repair device 200 with main stem 202 and distal branches 204 and 206. In this embodiment the branch 204 is affixed to the leading edge of the anterior leaflet 12. The second branch 206 is affixed to the underside of the anterior leaflet 12 as a secondary or strut chord. In this embodiment the leaflet edge is supported to set its position to achieve coaptation with the posterior leaflet 14 whose supporting chords are not shown. The secondary chord branch 206 provides support for the underside of the mitral valve leaflets and allows tension to be developed when between the cord and the leaflet at the annulus allowing flattening of the portion of the mitral valve which spans the left atrial orifice. The secondary chord 26 avoids billowing of the mitral valve which reduces the height of the valve and also reduces the coaptation length thereby reducing the function of the valve.

Figure 8D:
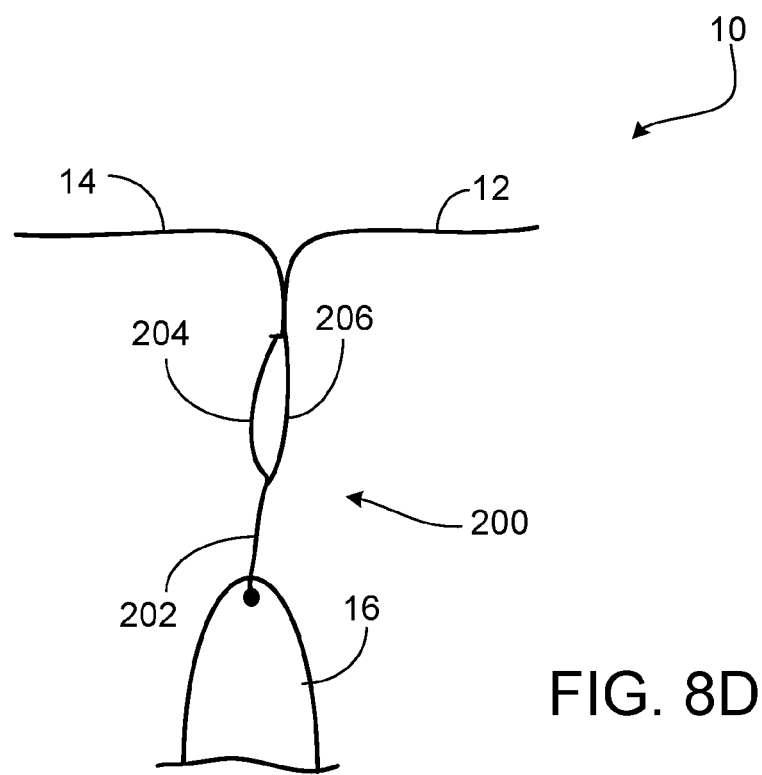
FIG. 8D shows a mitral valve with repair device.

Referring to FIG. 8D, a mitral valve 10 is shown in cross-section with anterior leaflet 12 and posterior leaflet 14. In a partial cut away view of the left ventricle the anterior papillary muscle 16 is shown. There is a repair device 200 with main stem 202 and branches 204 and 206. The main stem 202 is anchored to the anterior papillary muscle 16 and branches 204 and 206 are attached to the posterior leaflet 14 and anterior leaflet 12 respectively. Branches 204 and 206 are connected to the edges of the posterior and anterior leaflets to provide edge support. Some branches are used as secondary supports or combination of primary and secondary supports to one or both leaflets. Utilizing the repair device to support the leaflet edges or as secondary supports. During diastole the edges leaflets are separated by a distance covered by the length of the branches 204 and 206. This allows for improved inflow into the valve compared.

The repair device may be implanted as part of an open surgical repair of a valve or may be implanted as part of an interventional procedure, as discussed with references to FIGS. 17-21C. Surgical interventions may use, for example, an interventional catheter that positions the main stem within the ventricle and secures the main stem to a papillary muscle or the ventricular wall utilizing a variety of potential securement mechanisms including suture, clips, anchors, screw-based devices into the muscle, snares or other anchoring devices. The distal aspect of the main stem can be anchored near the annulus, at a second anchor point (annulus anchor point) including above or below the annulus In some repair devices, the main stem may be anchored to the ventricle or papillary muscle and one or more branches anchored to the valve leaflet, a the tip of the leaflet, or as a secondary or strut support.

Referring FIG. 9A, a repair device 200 includes the main stem 202 and the branches 204 and 206, and a distal aspect 208 of the main stem. The main stem 202 can be attached to the papillary muscle in a proximal aspect and near the annulus of the valve in the distal aspect 208. In one clinical situation, the two branches 204 and 206 are used to support the opposing sides of a commissure. Another clinical application of the repair device 200 is to use the distal aspect of the main stem 202 as a strut or secondary chord attached to the underside of the leaflet of the valve and the two branches 204 and 206 attached as edge chords to a valve leaflet. The two branches 204 and 206 could come off the main stem 202 at the same point or they could come off at different points even separated by a substantial difference depending upon the anatomy of the valve that is being repaired. The relative lengths of the branches 204 and 206 as well as the distal aspect of the main stem 208 that extends past the point where the branch branches emanate can vary in length and that length can be fixed by the device or can be modifiable by the surgeon during the time of implantation.

Referring to FIG. 9B, a repair device 220 includes a main stem 222 having distal aspect 228 of the main stem 222 and two branches 224 and 226. These branches 224 and 226 have loops which provide a fixed distance and means for the surgeon to attach the branches to a leaflet. Additionally, the distal aspect 228 of the main stem 22 is a loop. Some distal aspects are a linear element. The surgeon can quickly and easily secure the loops of the repair device 222 to the leaflet structures. The surgeon takes one or two bites of suture through the valve leaflet, papillary muscle, annulus, or other structure with a suture and secure it through the loop of the repair device. Similar to FIG. 8B, the proximal portion of the main stem can also be formed as a loop to facilitate implantation.

Figure 9C:
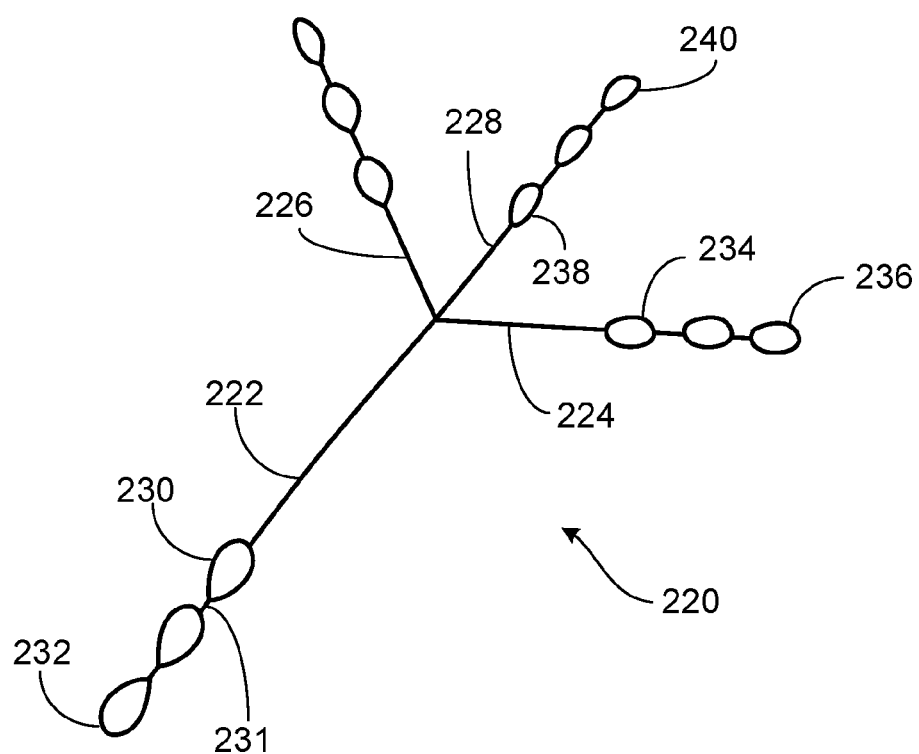

Referring to FIG. 9C, a repair device 220 includes a main stem 222 and branches 224 and 226 and a distal aspect 228 of the main stem 222. Branches 226, 224 include a series of loop elements 230. The main stem 222 includes an end loop element 232 on the proximal end of the main stem 222. These multiple loops 230 are connected by a connecting element 231. Some loop elements are arranged adjacent each other. These multiple loops elements allow intraoperative adjustment of the length based upon intraoperative measurements and other findings by the surgeon. The diameter of the loops varies from less than 1 mm inner diameter of the loop to 5 mm or more inner diameter. The surgeon selects a repair device where the intended target length of the main stem and branches corresponds with one or more middle loops. After initial implantation the surgeon then adjusts the length of the main stem branches by simply moving the securement of the leaflet or main stem to a different loop. Accordingly, in this embodiment the branches 224 and 226 also may have one or more loop elements 234 and 236 in the more proximal and distal aspect of the branches. As these loops provide some intraoperative adjustability, the distance between a distal inner aspect of each successive loop may be calibrated to a fixed known distance such as 1 mm apart or 2 mm apart. The distal aspect 228 of main stem 222 has a series of loops including one or more loops nearer to the main stem body 238 and a most distal loop 240. In this embodiment the distal aspect 228 of the main stem 222 can be trimmed to fit the loop element that is desired by the surgeon. The distal aspect 228 of the main stem 222 can also be used as a traditional branch. As in all of the embodiments, there may be one or two or more than two branches off of the main stem as is beneficial to achieve the desired anatomic result of the valve repair.

Figure 9D:
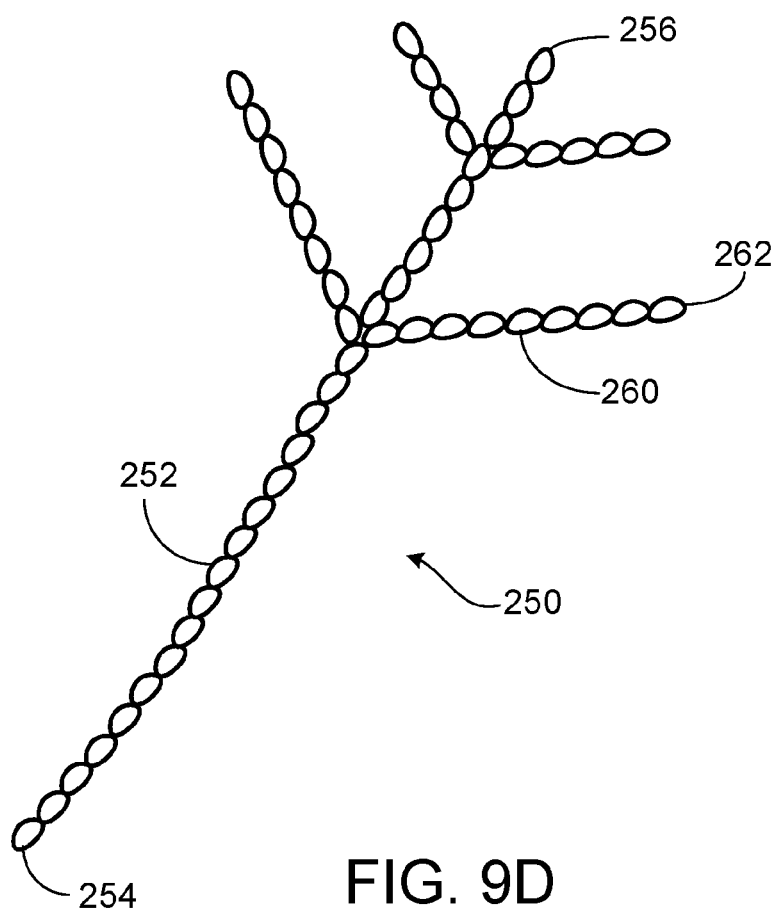

Referring to FIG. 9D, a repair device 250 has a main stem 252 a proximal aspect 254 (proximal end) and a distal aspect 256 (distal end). Emanating off the main stem 252 are one or more branches 260 with a distal aspect 262. The main stem 252 and for the branches 254 comprise connected adjacent loops or comprise a series of adjacent loops. The main stem 252 has a series of adjacent loops that extend the entire length of the main stem 252. In some main stems, the series of adjacent loops extend along a portion of the main stem 252. The branches 260 also comprise a series of intricate connected loops. Some branches comprise a combination of filaments or ribbon-like structures and some loops. Some branches include a defined distance between each loop or the loops.

In some applications of the repair device 250, the surgeon may elect to sew the repair device into the heart by fixing the more proximal aspect of the main stem 252 most proximal loop 254 and fix the distal end of the distal aspect of the main stem 252 near the valve annulus at or near the most distal loop 256. The branches can be sewn to the leaflet at the edge or strut cord position. Depending upon the supplied lengths of the branches in the dimensions of the valve, the surgeon can fix the leaflet to a loop. With passive testing, the surgeon assess the support provided by the repair device. If some the amount of adjustment is needed, the surgeon can elect to cut the suture attached to the repair device as needed and adjust and then reattached that to different loop to lengthen or shorten the main support such as one of the branches. Once the surgeon is satisfied with the function of the valve, the loops that extended past the loops that were fixed to the structures could be trimmed off. In one embodiment the repair device 250 may be created using laser cut PTFE or expanded PTFE sheets. The structure can best be made using a filament such as the suture or suture like material. The structure can also be created with other manufacturing approaches using biologic or non-biologic materials including 3D printing or injection molding.

Figure 9E:
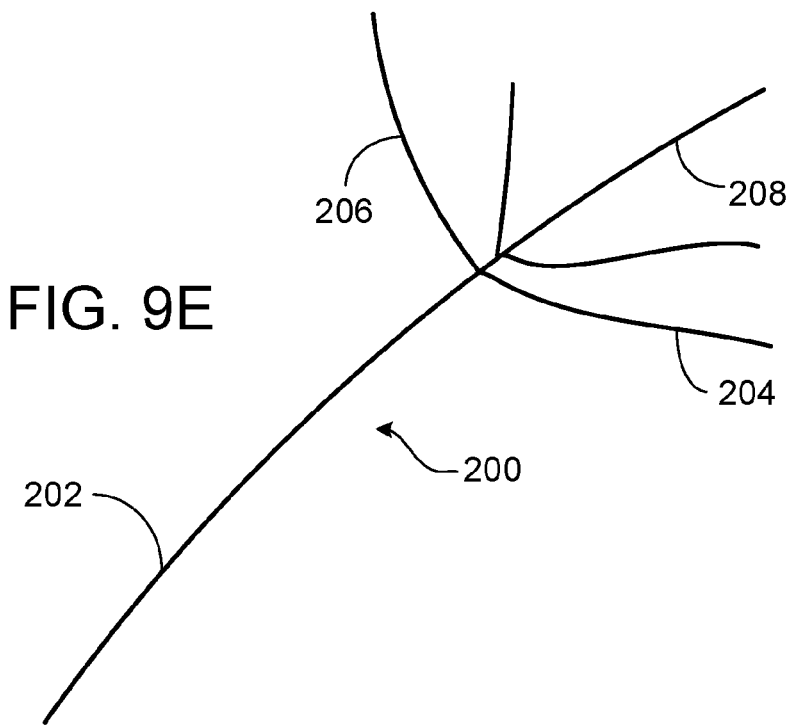
Figure 9F:
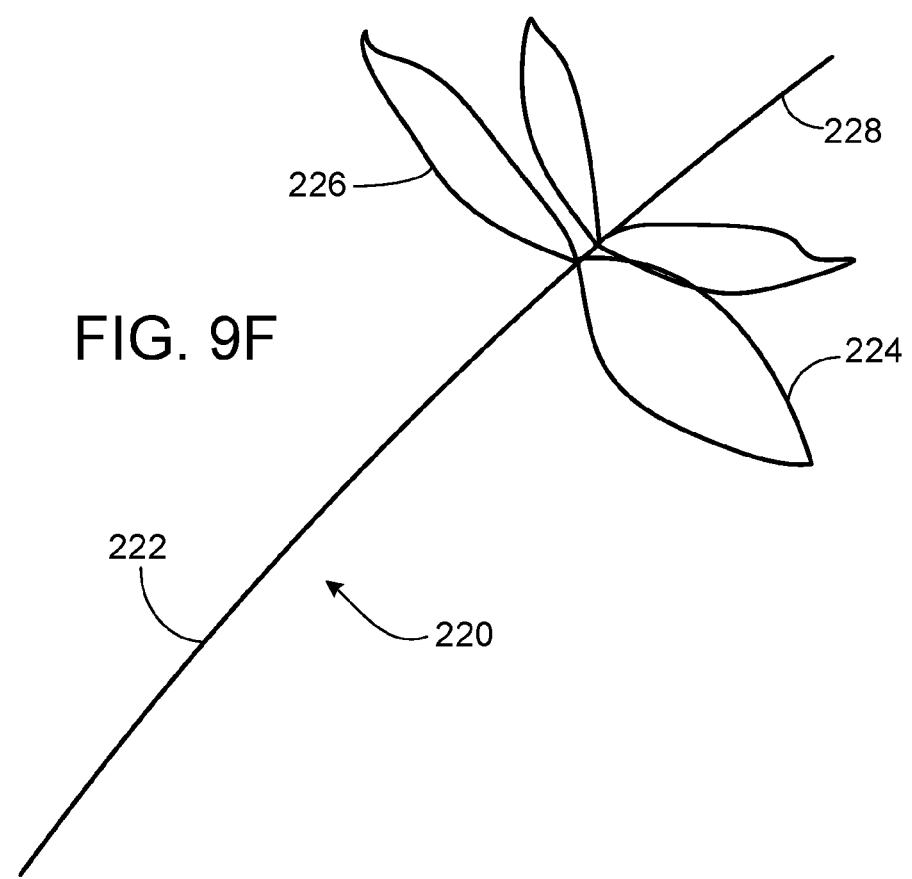

Referring to FIG. 9E, a repair device 200 includes main stem 202, distal aspect of the main stem 208. The main stem 202 has one or more branches 204, 206. The branches may be up to any conceivable number that would fit within the heart. These additional branches may originate from a very adjacent or same point on the main stem as other branches as shown in this embodiment. The branches may alternatively emanate from any portion of the main stem including the very proximal aspect of the main stem. Referring to FIG. 9F, a repair device 220 has a main stem 222 and the distal aspect 228 to the main stem 222. There are multiple branches to 224 and 226 which emanate from the main stem in the configuration of loops. There may be a combination of branches emanate from a single point or on multiple fronts off the main stem. This could include the very proximal most aspect of the main stem. Clearly the device can be a combination of filament and loop extensions that emanate from the main stem.

Figure 10A:
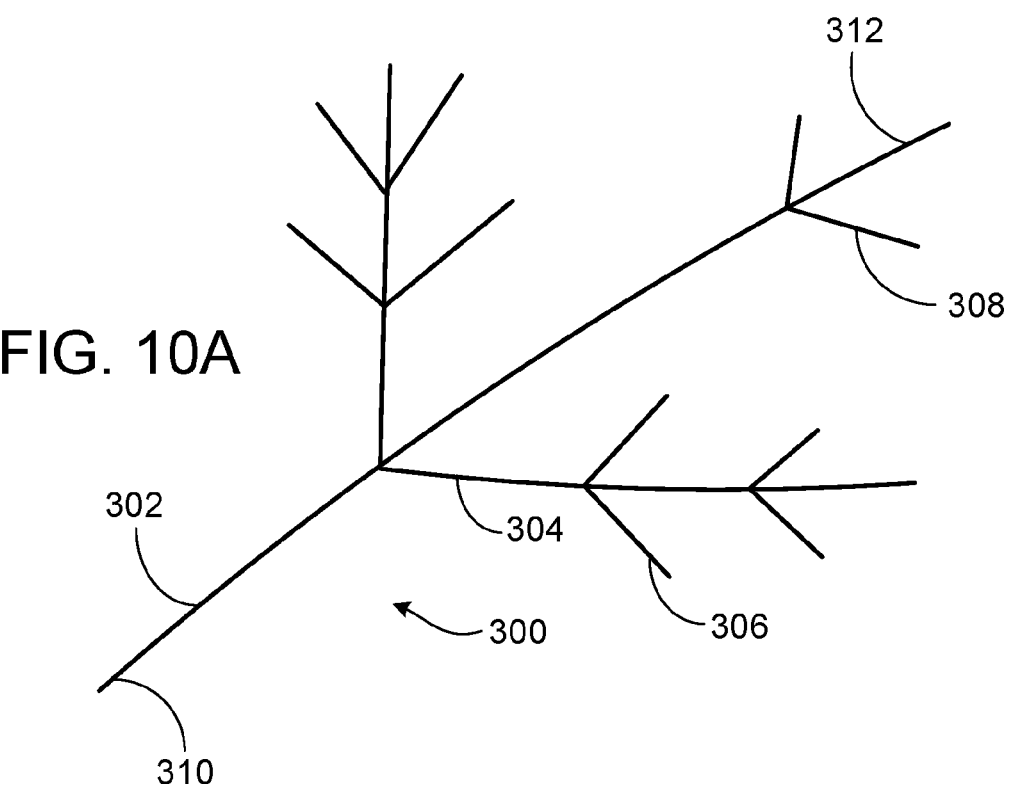
FIGS. 10A and 10B show example repair devices.

Referring to FIG. 10A, a repair device 300 includes a main stem 302 that includes proximal end 310 and distal end 312. Connected to the main stem 302 are branches 304, 308. The branches 304 may have one or more additional sub-branches 306 extend from the branch 304. The branch 304 is a first order branch and the branches 306 are second order branches or sub-branches. One can see that any conceivable complexity of first, second, third or fourth order branches could be considered off of one or more main stem branches. Some repair devices include any combination of simple branches and more complex branches with second and third order branches themselves. Each of these branches can be configured in with linear elements and or loop elements in various combinations, for example, multiple loop elements in succession as described in FIG. 9C and FIG. 9D.

The first order branch 304 extends in a first direction. The a different first order branch 305 extends in a second direction. In repair device 300, the first and second direction are different. In some repair devices the first and second direction are parallel. The sub branch 306 extends in a direction different from both the first and the second direction. Some sub branches extend in a direction parallel to the first or second direction.

Figure 10B:
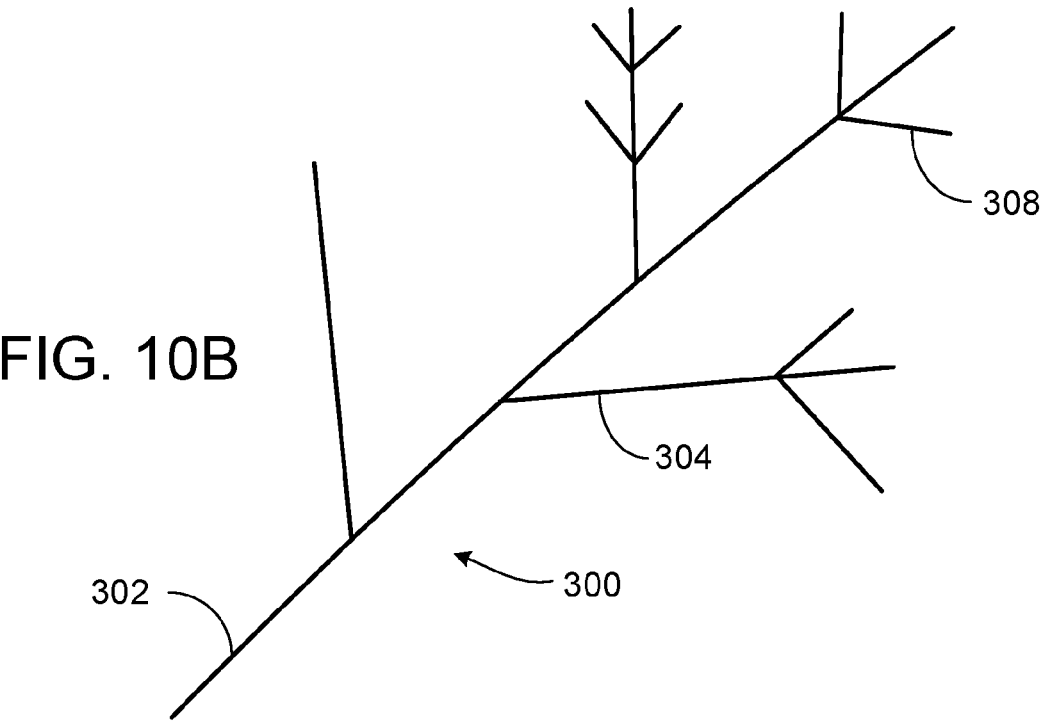

Referring to FIG. 10B, a repair device 300 includes a main stem 302 and multiple branches including 304 and 308. The repair device 300 has combination of branches which includes simple branches (first order branches) or branches with a second or higher order (sub-branches) off themselves.

Figure 11:
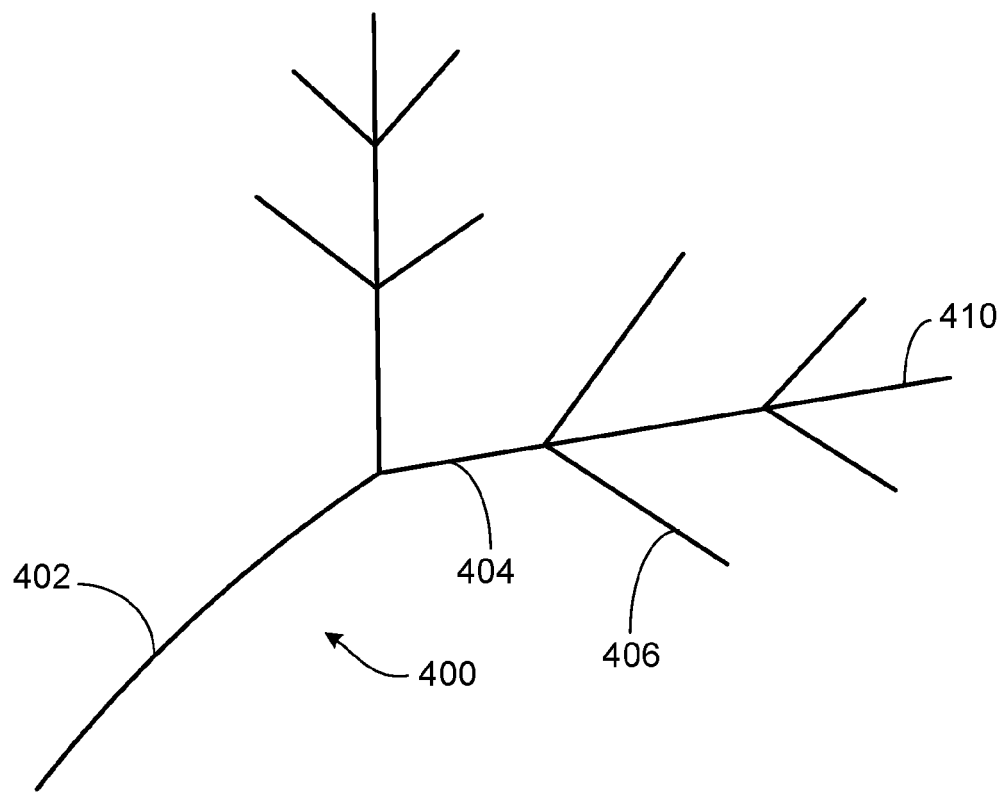
FIG. 11 shows an example repair device.

Referring to FIG. 11, a repair device 400 includes a main stem 402 and branches 404, 406. The first order branch 404 has successive second order branches 406 as well as the distal aspect 410 of the branch 404. Some second order branches have additional higher order branches. A clinical application of a the repair device 400 may be a commissure that needs to be supported and a separate cleft in the anterior or posterior leaflet of the mitral valve or one of the leaflets of the tricuspid valves nearby the commissure. The proximal aspect of the main stem 402 is be anchored to a papillary muscle within the ventricle using a papillary anchor. The distal aspect 410 of the branch 404 anchored near the annulus of the valve using a annulus anchor. The second order branches 406 off the first order branch 404 (main branch) are anchored to opposing sides of a commissure and support the commissure and the adjacent cleft to allow for adequate coaptation of the leaflet structures without inhibiting the inflow of the valve.

Figure 12A:
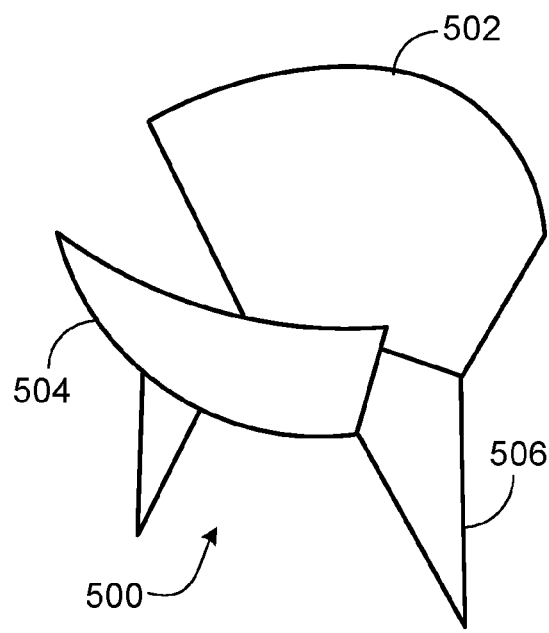
FIGS. 12A and 12B show computer models of a mitral valve.
Figure 12B:
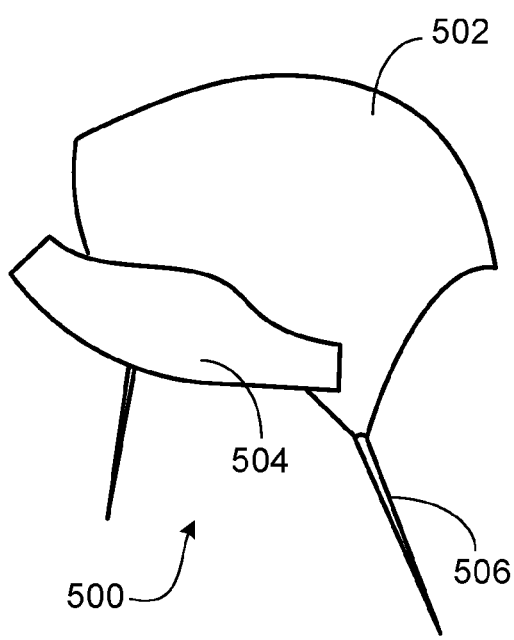

Referring to FIG. 12A, a computer model of a mitral valve 500 is shown with anterior leaflet 502, posterior leaflet 504 in the open position during diastole, and the multiple supporting chords 506. This computer model was generated to model the mechanics of valve function in particular the contribution of the chords to control coaptation and coaptation height to allow adequate valve function. Referring to FIG. 12B, a computer generated mitral valve model 500 with anterior leaflet 502 and posterior leaflet 504 with supporting chords 506 in a closed valve configuration during ventricular systole shows where there is coaptation between the anterior leaflet 502 and posterior leaflet 504.

Figure 13A:
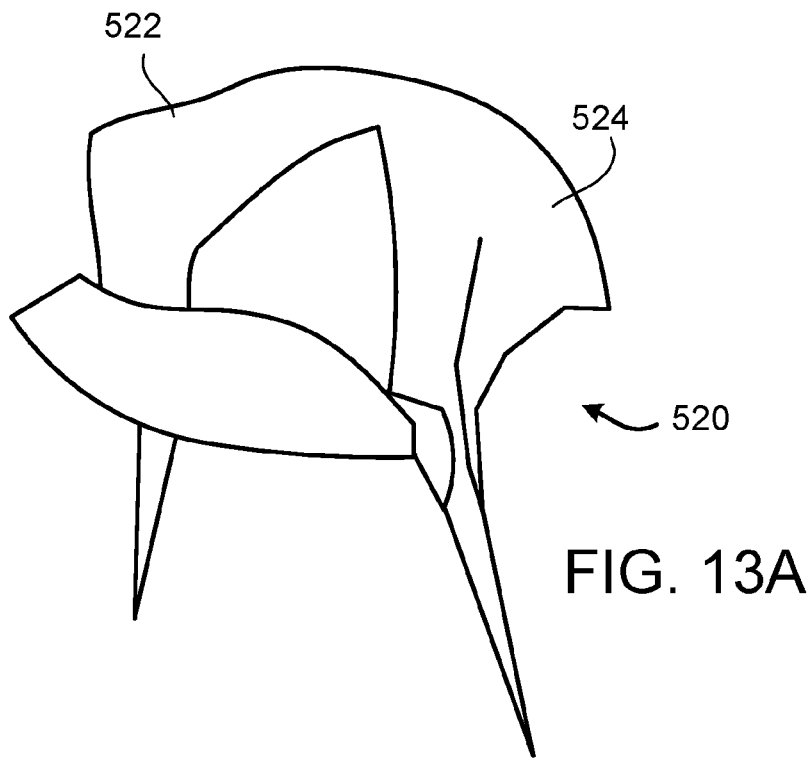
FIGS. 13A-13C show computer models of a mitral valve
Figure 13B:
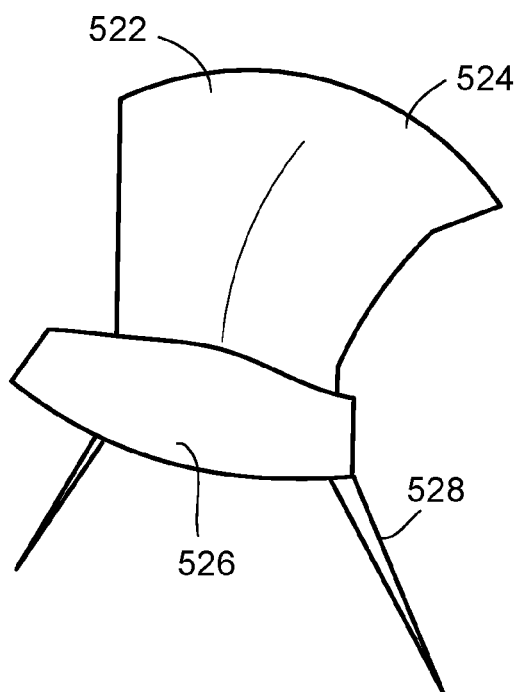

Referring to FIG. 13A, a computer model of the mitral valve 520 has a cleft in the anterior leaflet creating a superior bridging leaflet 522 and inferior bridging leaflet 524 with mural leaflet 526 supported by multiple chords 528. In this figure, the valve is in the diastolic position with a cleft wide open. Referring to FIG. 13B, the computer model of the mitral valve with superior bridging leaflet 522 inferior bridging leaflet 524, and mural leaflet 526 is now shown in the closed position with the cleft closed with adequate coaptation of the cleft and the anterior-posterior leaflets are also demonstrating adequate coaptation. The cleft is supported by a repair device 50.

Figure 13C:
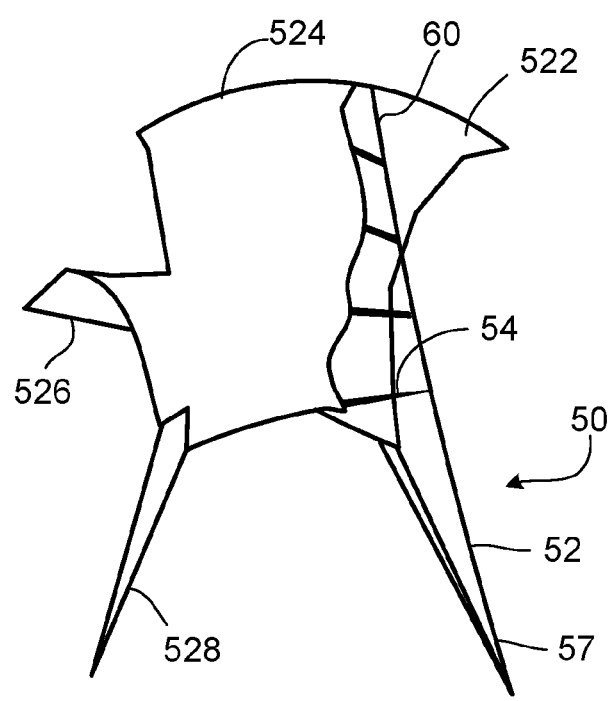

FIG. 13C shows an isometric view of the mitral valve 500 with superior bridging leaflet 522 and inferior bridging leaflet 524 and mural leaflet 526 with supporting native chords 528. The repair device 50 has the proximal end 57 anchored to the papillary muscle and main stem 52 with distal portion 68 of the main stem 52 attached to the annulus of the anterior leaflet. There are multiple branches 54 which extend to both the superior and inferior bridging leaflets 522, 524 along the length of the cleft. The repair device 50 includes four pairs of branches 54 that extend from the main stem 52 to the superior and inferior bridging leaflets 522, 524. As the ventricle contracts and the mitral valve 500 closes during systole the branches 54, supported by the main stem 52 impart forces on the leaflets 522, 524, 526 resulting in closure of the cleft with adequate coaptation height.

Figure 14:
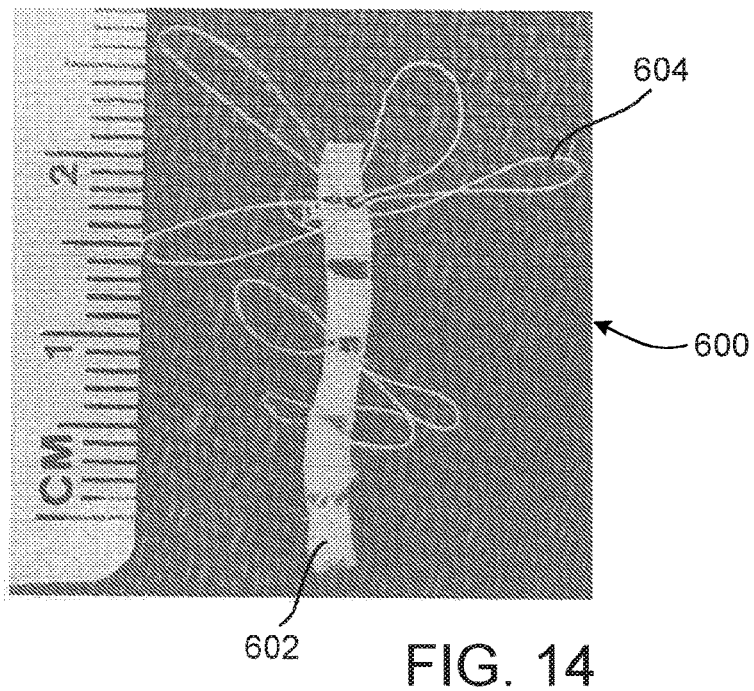
FIG. 14 is a photograph of a repair device.

FIG. 14 shows a picture of a repair device 600 with the main stem 602 and branches 604. In this configuration, the main stem 602 is created with a strip of the 1 mm thick expanded PTFE sheet material. There are four pairs of branches 604 emanating from the main stem 602. Each of these branches 604 are with 7-0 PTFE suture. The suture is affixed to the main stem 602.

Figures 15A, 15B:
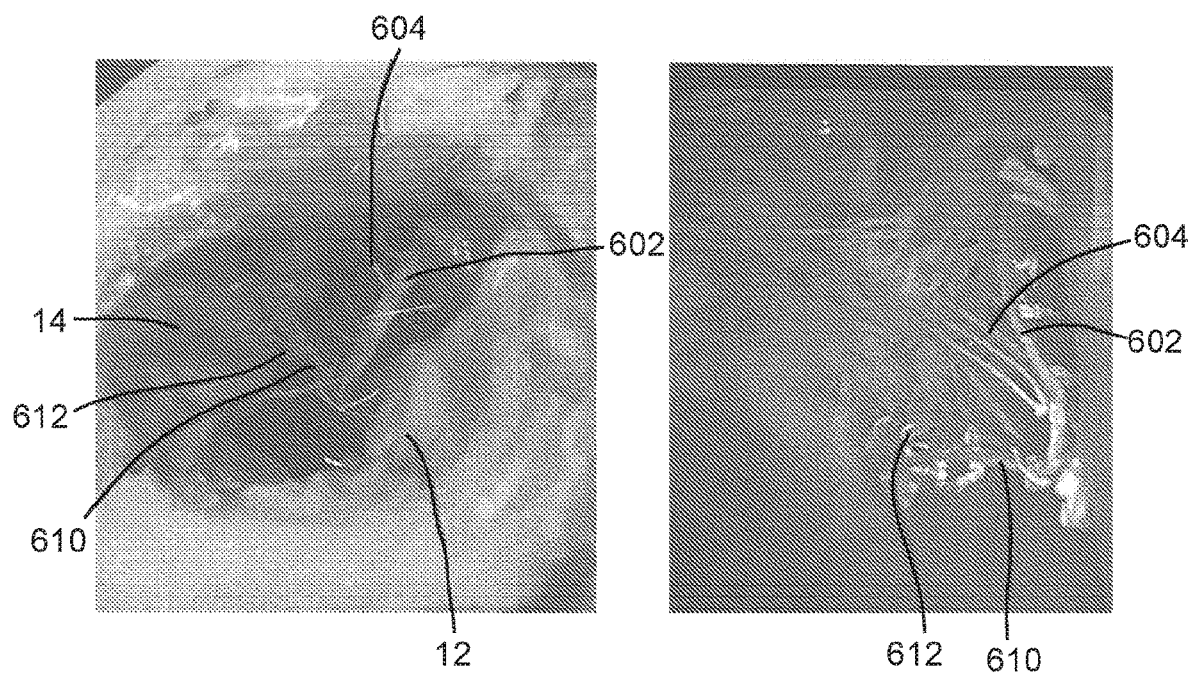
FIG. 15A is a picture of a porcine mitral valve from the atrium with leaflets supported by a repair device.
FIG. 15B is a picture of a porcine mitral valve from the ventricle with leaflets supported by a repair device.

FIG. 15A shows a picture of a porcine mitral valve of an explanted porcine heart with the anterior leaflet 12 and posterior leaflet 14. In this in vitro experiment, the entire native chordae support structure for the anterior and posterior leaflets was surgically excised. This left the valve completely unsupported with flail anterior and posterior leaflets. Branched chordae support devices similar to that seen in FIG. 14 were implanted to support the leaflets. In this configuration a repair device with main stem 602 and branches 604 was positioned between the anterior papillary muscle and the annulus of the mitral valve adjacent to the anterior commissure. The main stem 52 was affixed to the papillary muscle using the papillary anchor (not shown) and affixed to the annulus using the annulus anchor (not shown). The branches 604 were affixed to the anterior-posterior leaflets along the anterior commissure to support the commissure during valve closure. The most proximal branches extended medially on the posterior leaflet and the medial aspect of the anterior leaflet to support the anterior leaflets. An adjacent cleft is located between in the posterior leaflet. This cleft was supported by a separate repair device with main stem 610 and branches 612. These this was affixed to the edges of P1 and P2 leaflets along the cleft to support closer those leaflets during systole. In this experiment there were two additional branched chordae support devices placed on the posterior papillary muscle extending to the annulus for main stem support and the support of the posterior commissure and the cleft between the P2 to P3 segments of the posterior valve leaflet. With these four branched chordae support devices in place there was function of the mitral valve leaflet with adequate coaptation and minimal regurgitation by passive testing. Referring to FIG. 15B, this is a picture of the inside of left ventricle of an in vitro porcine heart model as described above where all the chordae supports from the native papillary muscle to the leaflets had been divided and excised. The leaflets were completely supported by repair devices. As seen here in experimental systole with the ventricle pressurized with water retrograde via the aorta, there are two repair devices one with main stem 602 and branches 604 and another with the main stem 610 and branches 612. These devices supported the entire valve anterior and posterior leaflets and allowed effective coaptation with minimal regurgitation during passive testing.

These repair devices have been tested in an in vivo porcine model of a cleft mitral valve. These experiments have been performed in porcine animals in the range of 50 to 60 kg. The animal was placed on cardiopulmonary bypass and with the heart arrested and mitral valve exposed, a cleft was created in the anterior leaflet of the mitral valve which extend nearly the complete length of the anterior leaflet. The annulus of the mitral valve was downsized both with a commissuroplasty type stitch in the annulus of the mitral valve adjacent to the tip of the incision in the mitral valve leaflet that comprised the cleft. The stitch provided some initial coaptation of the edges of the cleft in the mitral valve to simulate what is seen in a normal cleft mitral valve congenital defect. The annulus of the mitral valve was also downsized with an annuloplasty. In this model, severe mitral valve insufficiency was demonstrated by passive testing and also by echocardiographic evaluation once the animals was weaned off bypass. These animals had elevated left atrial pressures with the mitral valve cleft after creation and prior to attempted to surgical repair the level of 12-18 mmHg. These animals were placed back on a cardiopulmonary bypass and the created cleft in the anterior leaflet of the mitral valve was supported by a repair device. The proximal aspect (proximal end) of the main stem of the repair device was affixed to the anterior papillary muscle with a pledgeted 5-0 suture. The distal aspect (distal end) of the main stem was attached to the mitral valve annulus near the tip of the created cleft. The length of the main stem and the multiple branches were estimated by echocardiographic measurements taken before and after creation of the cleft with the animal off heart lung machine. These measurements were confirmed with the heart open, and the repair device was sewn in place with multiple branches supporting the opposing aspects of the mitral valve anterior leaflet along the newly created cleft. By passive testing, the repair device supported cleft closure and the effect was good mitral function with minimal regurgitation. The animals went off cardiopulmonary bypass and demonstrated acceptable mitral valve function with trivial to mild mitral valve regurgitation seen in most animals after coming off bypass and out to three hours after weaning off bypass. In these in vivo experiments, numerous configurations of the repair device had been tested and proven effective. The embodiment shown in FIG. 14, the main stem includes PTFE and loops of the PTFE for the branches has been the most common tested embodiment.

Figure 16:
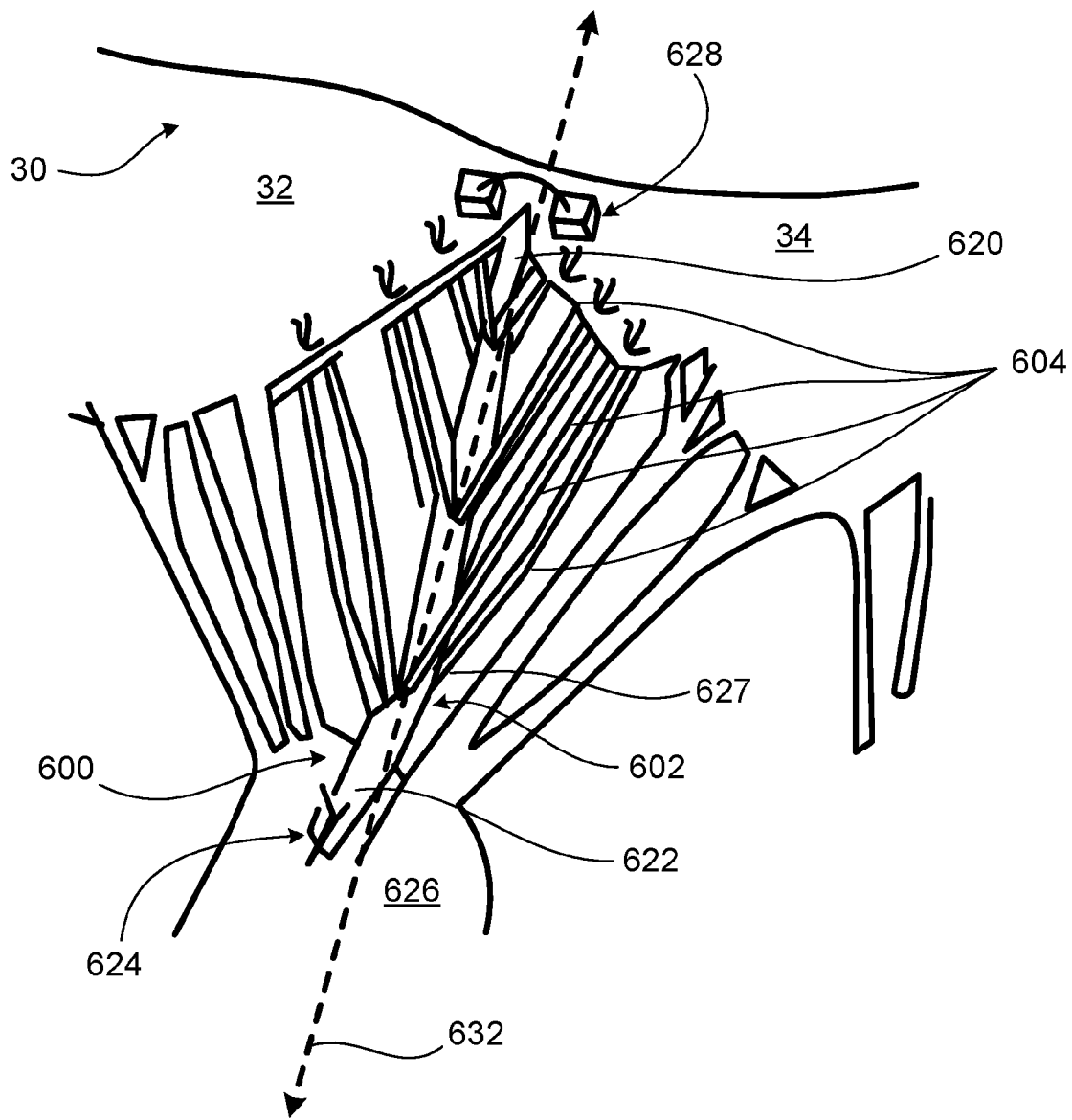
FIG. 16 shows a view of a repair device connected to leaflets of the mitral valve.

FIG. 16 shows a view of the repair device 600 connected to leaflets 32, 34 of the mitral valve 30. The repair device 600 includes the main stem 602 and the branches 604. The main stem 602 has a distal end 620 and a proximal end 622. The main stem 602 also includes a papillary anchor 624 on the proximal end 622. The papillary anchor 622 attaches the main stem 602 to a papillary muscle 626. The papillary anchor 622 attached to papillary muscle 626 such that the repair device 600 is translationally coupled to the papillary muscle 626. The main stem 602 also includes an annulus anchor 628 that attaches the distal end 620 of the main stem 602 to an annular portion 630 of the valve 30 using an annulus anchor 634. The annular portion 630 shown in FIG. 16 is a commissural leaflet. The branches 604 are made of string or suture. The branches 604 are connected to the leaflets 32, 34 using suture.

The device 600 has a relaxed position and a flexed position. FIG. 16 shows the repair device 600 in the relaxed position. In this position, the papillary muscle 626 is relaxed. The branches 604 are untensioned and limp. In this configuration, the mitral valve 30 is open and blood flows through the interior space between the relaxed leaflets 32, 34. To close the mitral valve 30 and move into the flexed position, the papillary muscle 626 contracts and moves downwards. The papillary anchor 624 moves with the papillary muscle 626 and pulls the main stem 602 away from the leaflets 32, 34. The main stem 602 pulls the branches 604 away from the leaflets 32, 34. The branches 604 become tensioned and taut. The main stem 602 continues to pull the branches 604 so that the taut branches 604 move with the main stem 602. The branches 604 rotate about a fixation area 627 on the main stem 602 to become increasingly parallel to the main stem 602, or a longitudinal axis 632 of the main stem 602. The branches 604 also translate with the main stem 602 due to the attachment of the branch 604 and main stem 602 at the fixation area 627. The movement of the branches 604 to become increasingly parallel to the main stem 602, moves the leaflets 32, 34 towards each other. At full contraction of the papillary muscle 626, the leaflets 32, 34 abut and the valve 30 is closed. The repair device 600 is in the flexed position when the papillary muscle 626 is fully contracted. In some repair devices, the valve is remains slightly open in the flexed position.

FIGS. 17A-17D show the repair device in use during a surgery to correct a stenotic mitral valve 30. FIG. 17A shows a stenotic mitral valve 650 with a small mitral valve orifice 652. To correct the mitral valve 650, the surgeon enlarges the mitral valve orifice 652 but cutting through leaflet tissue 654, as shown in FIGS. 17B and 17C. At this step, the mitral valve 650 has an orifice of proper size, however the leaflet tissue 654 is unsupported by chords. The valve therefore may not open or close properly. Mitral regurgitation may also occur due to the unsupported leaflet tissue 654. Two repair devices 600 are attached to the leaflet tissue 654 and to a papillary muscle (not shown) to properly open and close the mitral valve 6501 and reduce mitral regurgitation.

Figure 18:
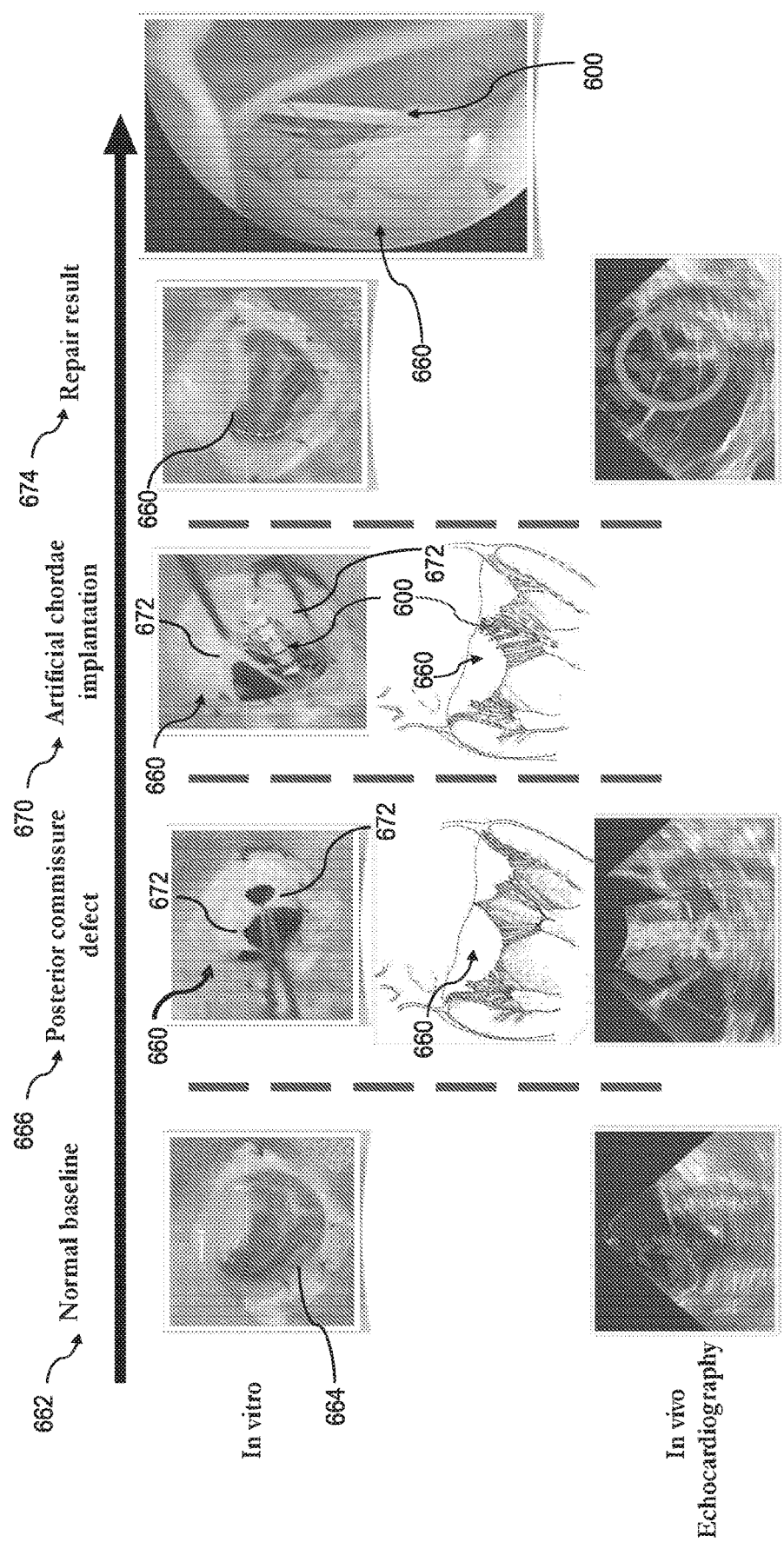
FIG. 18 shows a repair device in use during a surgery.
Figure 19:
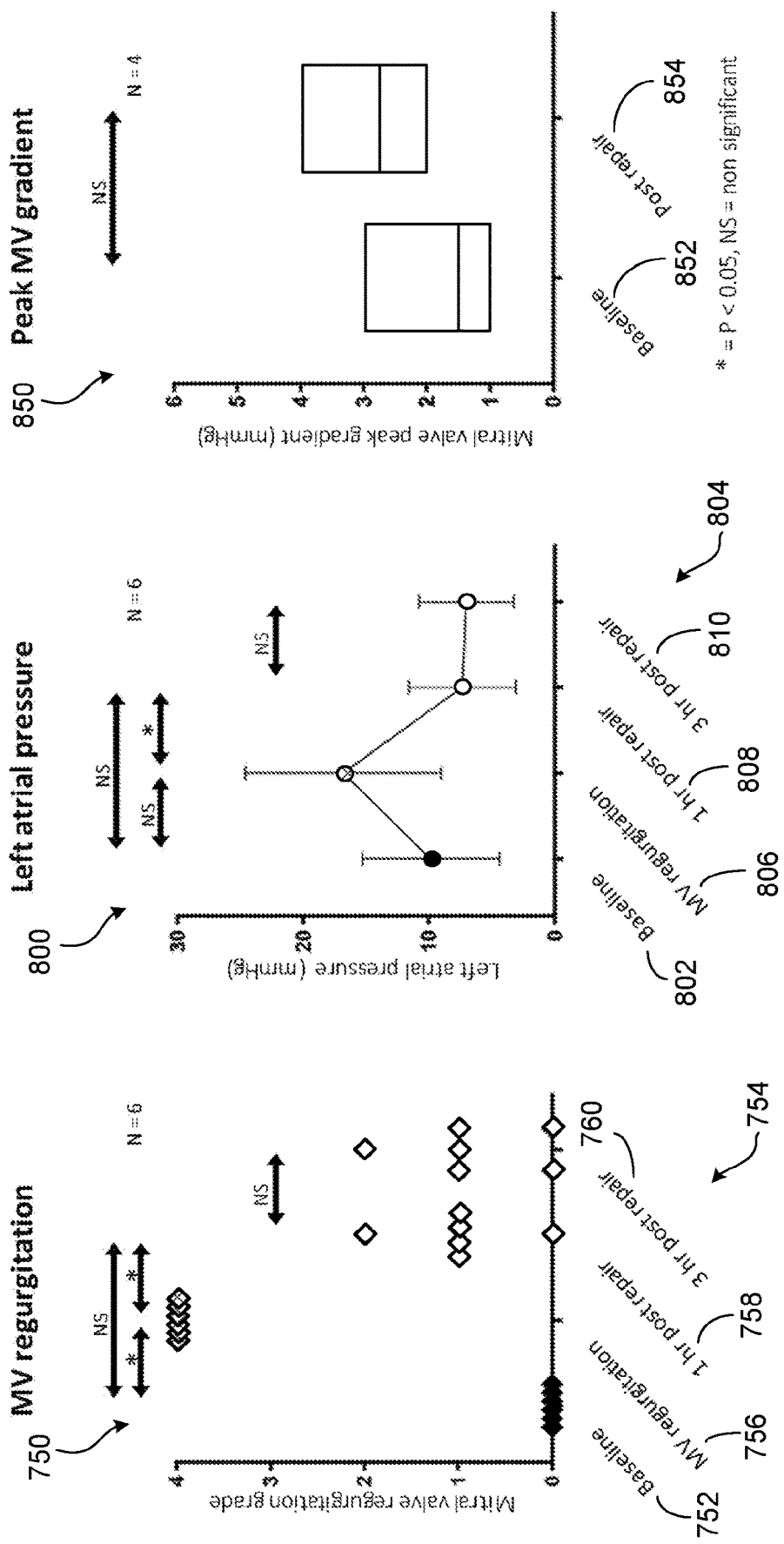
FIGS. 19A-19C show data generated by testing a mitral valve repaired as shown in FIG. 18.

FIG. 18 shows the repair device 600 in use during a surgery to repair a commissure prolapse of a mitral valve 660. The experiment was performed using an in-vivo swine model. The repair device 600 in use during a surgery to repair a cleft of the mitral valve. The normal baseline column 662 shows a normal mitral valve 664 in the flexed/closed position. An Echocardiogram also shows a baseline image for reference. The posterior commissure defect column 666 show the mitral valve 660 with a commissure defect in the closed position. The column 666 also includes a drawn diagram of the commissural defect and an echocardiogram image of the defect. The artificial chordae implantation column 670 shows an image and a drawing of the repair device 600 being implanted into a heart. To implant the device, the papillary anchor 624 is attached to the papillary muscle. This can be done using suture, or any other attachment technique. The branches 604 are attached to leaflets 672 of the mitral valve 660 using suture. The repair result column 674 shows the repair device in the flexed position and the according echocardiogram. The normal baseline column 662 shows a normal mitral valve 664 in the flexed/closed position. An Echocardiogram also shows a baseline image for reference. The posterior commissure defect column 666 show the mitral valve 660 with a commissure defect in the closed position. The column 666 also includes a drawn diagram of the commissural defect and an echocardiogram image of the defect. The artificial chordae implantation column 670 shows an image and a drawing of the repair device 600 being implanted into a heart. To implant the device, the papillary anchor 624 is attached to the papillary muscle. This can be done using suture, or any other attachment technique. The branches 604 are attached to leaflets 672 of the mitral valve 660 using suture. The repair result column 674 shows the repair device in the flexed position and the according echocardiogram.

Referring to FIGS. 19A-19C, an in-vivo experiment to test a mitral valve repaired as shown in FIG. 18 was performed. The repair device used is comprised of a 2 to 3 mm width polytetrafluoroethylene (PTFE) strip as the main stem and 7/0 PTFE sutures used to form loops as paired branches fixed to the main stem. This design is similar to repair device 600. Adult Yorkshire pigs were used to evaluate the performance of the repair device in repairing a commissure prolapse. Performance was assessed by measuring mitral valve regurgitation, left atrial pressure, and peak mitral valve gradient were measured over time. The commissure prolapsed mitral valve was repaired in adult Yorkshire pigs in-vivo using cardiopulmonary bypass (CPB). In Group I(GI), posterior commissural prolapse was created by severing all repair devices the leaflet of the valve. After weaning from the first CPB run, epicardial echocardiography was used to assess mitral valve function and to determine the appropriate length of repair device. During the second CPB, the main stem of the repair device was implanted between the closest papillary muscle and the mitral annulus behind the commissure. The PTFE loops were attached to the leaflets of the mitral valve using 6/0 polypropylene sutures. Following implantation, a foldoplasty stitch was placed at the tip of the commissure to initiate adequate leaflet coaptation. Measurements were taken prior to implantation of the repair device to assess the severity of the defect. Post repair measurements were taken 1 hour after repair and 3 hours after repair to assess the performance of the repair device. Mitral valve competence was assessed by analysis of the echocardiographic regurgitant vena contracta.

The experiment as described previously was conducted using six adult pigs (N=6). Each of the graphs 750, 800, and 850 show a baseline 752, 802, 852 data set and a post repair 754, 804, 854 data set(s). The baseline 752, 802, 852 data sets are generated by measuring the mitral valve regurgitation, left atrial pressure, peak mitral valve gradient of a normal valve. The baseline measurements are taken using a defect-free valve similar to the valve 664 in FIG. 18. Graphs 750 and 800 also show a mitral regurgitation data set 756, 806 that is measured after creating the commissure, before implanting the repair device. The mitral regurgitation data set 756, 806 measurements are taken using a valve similar to the defected valve 600 in FIG. 18 on the posterior commissures defect column 666. The post repair data sets 754, 804, 854 include data measured 1 hour post repair 758, 808 and 3 hours post repair 760, 810. The post repair data sets 754, 804, 854 measurements are taken using a valve similar to the repaired valve 600 in FIG. 18 on the repair result column 674.

Graph 750 shows the severity of the mitral valve regurgitation grade (degree of mitral valve leak) vs. the baseline data set 752, the mitral valve regurgitation data set 756, the 1 hr post repair data set 754, and the 3 hr post repair data set 760 for each of the 6 test pigs. The grades on the y-axis range from a minimum of 0 (no leak), 1 (trivial), 2 (mild), 3 (moderate to maximum), and 4 (open or massive leak). In the baseline data set 752 the six mitral valves of the test pigs have no leak (grade 0). The commissure prolapse results in a grade 4 leak as shown in the mitral valve regurgitation data set 756. The repair device is then implanted to correct the commissure prolapse. The post repair data sets 754 show the leak reduced to trivial (grade 1) or no leak (grade 0) in 5 test pigs and one test pig to mild (grade 2) after 1 hr and 3 hrs post repair. This reduction in the leak grade was statistically significant ($p<0.05$).

Graph 800 shows the left atrial pressure (mmHg) vs. the baseline data set 802, the mitral valve regurgitation data set 806, the 1 hr post repair data set 804, and the 3 hr post repair data set 810 for each of the 6 test pigs. The data sets, 802, 806, 808, 810 show the change in left atrial pressure in mmHg during same time line point as graph 750. The left atrial pressure increased from the baseline measurements to the mitral valve regurgitation measurements. The mitral valve regurgitation data set 806 was measured during the grade 4 leak directly after the commissure prolapse was surgically induced or formed. After the repair device was implanted, the left atrial pressure significantly ($p<0.05$) reduced to normal levels in the 1 hr post repair data set 808 and remained the in the 3 hr post repair data set 810.

Graph 850 shows the mitral valve peak gradient (mmHg) vs. the baseline data set 852 and the post repair data set 854. In this test only four of the six test pigs were evaluated (N=4). The mitral valve peak gradient helps to evaluate the mitral valve orifice for any stenosis after implanting the repair device. A repaired valve with no significant change in the peak gradient indicates that the repair device did not critically shrink the valve orifice. There was no significant change in the peak gradient across the valve between the normal valve at baseline 852 and after implantation (post repair 854).

In GI, complete repair was achieved with three pairs of PTFE branches. All test pigs had absent or trivial mitral valve regurgitation during 3 hrs of recovery. No mitral valve gradient or leaflet restriction was observed in either GI.

Figure 20:
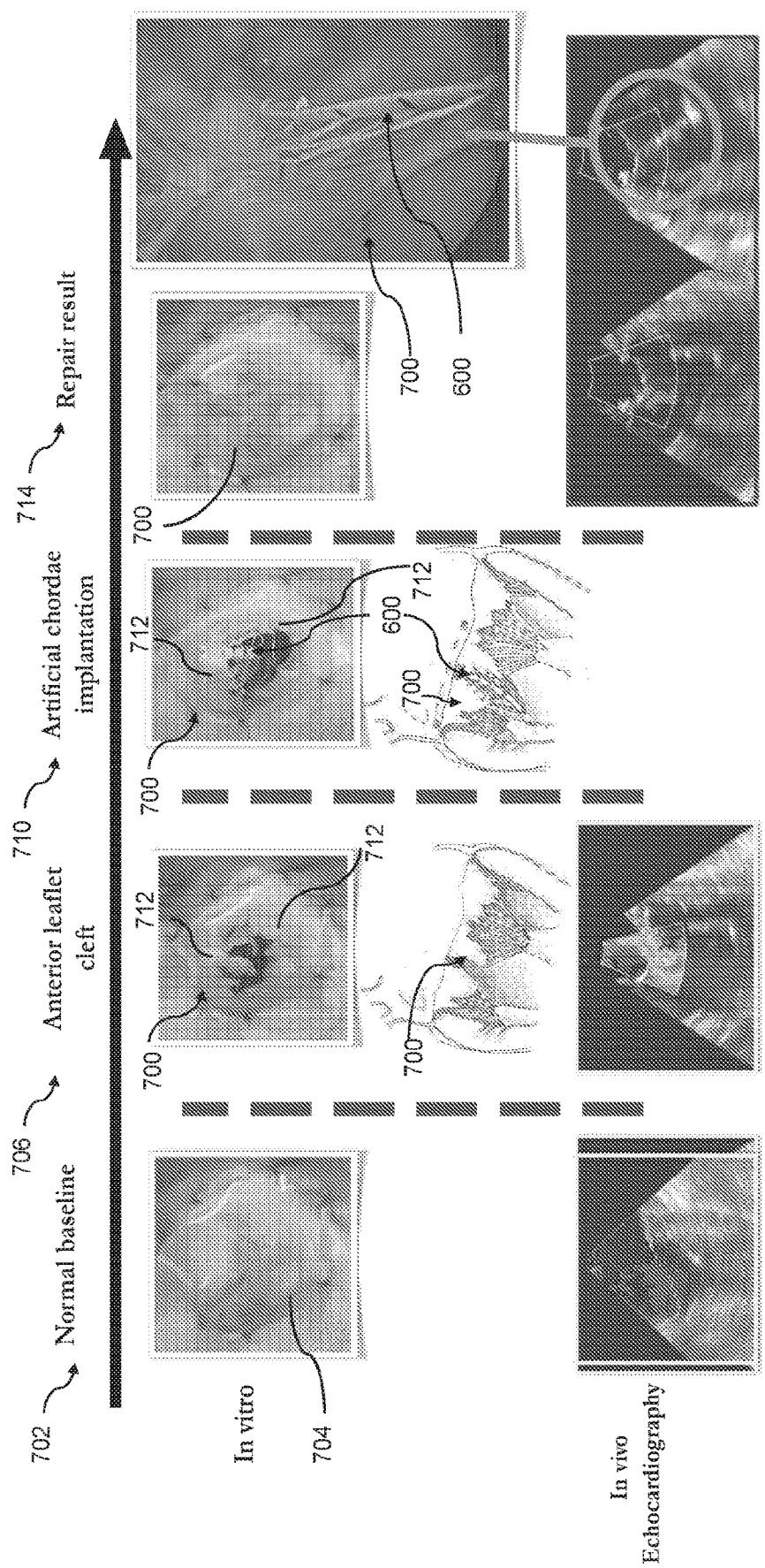
FIG. 20 shows a repair device in use during a surgery.

FIG. 20 shows the repair device 600 in use during a surgery to repair a cleft of the mitral valve 700. The experiment was performed using an in-vivo swine model. The normal baseline column 702 shows a normal mitral valve 704 in the flexed/closed position. An Echocardiogram also shows a baseline image for reference. The anterior leaflet cleft column 706 show the mitral valve 700 with a cleft in the closed position. The column 706 also includes a drawn diagram 708 of the cleft and an echocardiogram image of the defect. The artificial chordae implantation column 710 shows an image and a drawing of the repair device 600 being implanted into a heart. To implant the device 600, the papillary anchor 624 is attached to the papillary muscle. This can be done using suture, or any other attachment technique. The branches 604 are attached to leaflets 712 of the mitral valve 700 using suture. The repair result column 714 shows the repair device in the flexed position and the according echocardiogram.

Figures 21A, 21B, 21C:
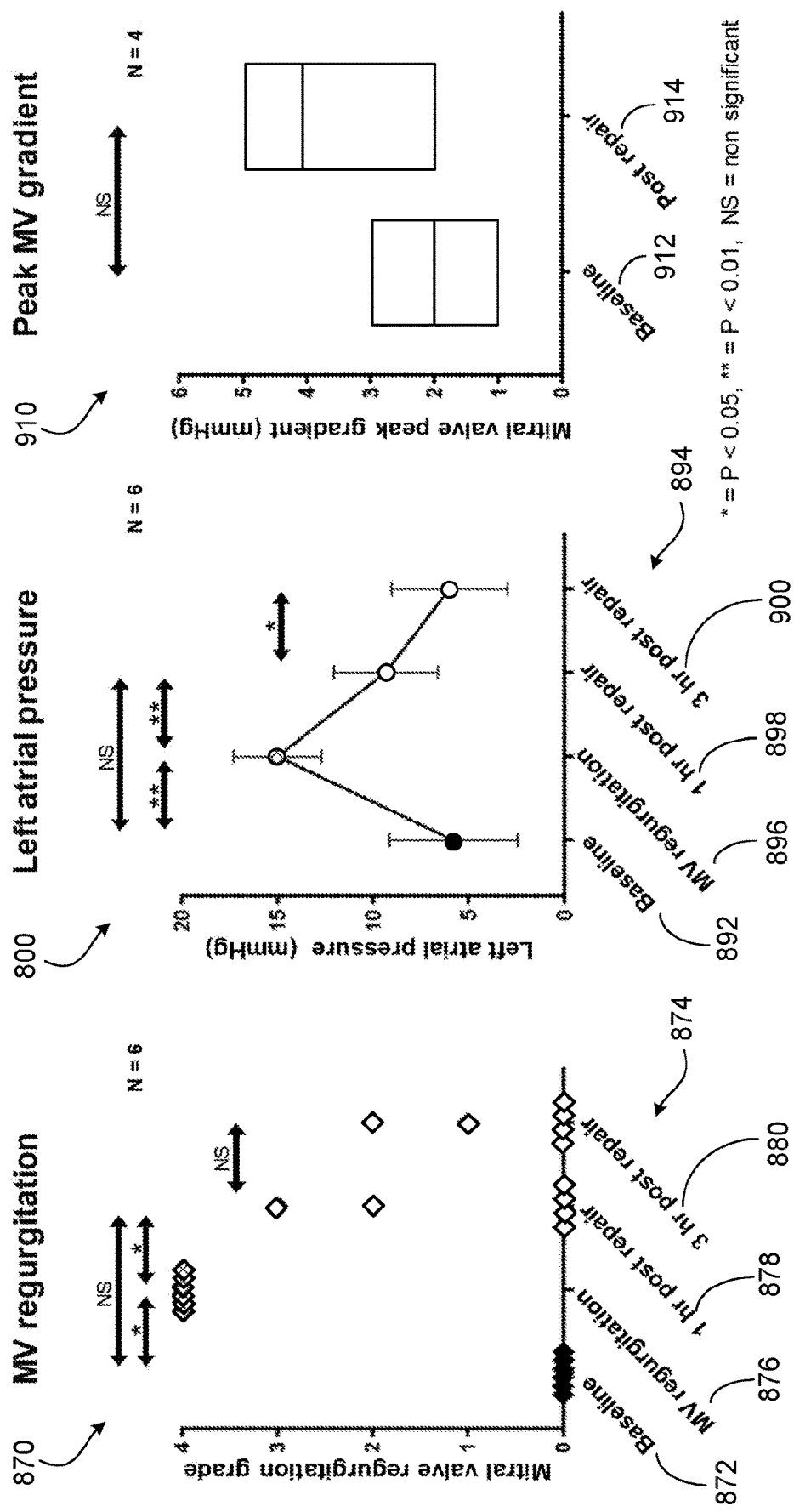
FIGS. 21A-21C show data generated by testing a mitral valve repaired as shown in FIG. 18.

Referring to FIGS. 21A-21C, an in-vivo experiment for testing a mitral valve repaired as shown in FIG. 20 was performed. The repair device used is comprised of a 2 to 3 mm width polytetrafluoroethylene (PTFE) strip as the main stem and 7/0 PTFE sutures used to form loops as paired branches fixed to the main stem. This design is similar to repair device 600. Adult Yorkshire pigs were to evaluate the performance of the repair device in repairing a cleft. Performance was assessed by measuring mitral valve regurgitation, left atrial pressure, and peak mitral valve gradient were measured over time. The cleft in the mitral valve was repaired in adult Yorkshire pigs, in-vivo using cardiopulmonary bypass (CPB). In Group II (GII) the cleft was created by splitting anterior leaflet at A2 up to 70%-80% of the leaflet height. Additionally, in GII a complete flexible Dacron ring annuloplasty was performed simultaneously. After weaning from the first CPB run, epicardial echocardiography was used to assess mitral valve function and to determine the appropriate length of the repair device. During the second CPB, the main stem of the repair device was implanted between the closest papillary muscle and the mitral annulus behind the cleft. The PTFE loops were attached to the leaflets of the mitral valve using 6/0 polypropylene sutures. Following implantation, a foldoplasty stitch was placed at the tip of the cleft to initiate adequate leaflet coaptation. Measurements were taken prior to the first CBD to establish a baseline. Measurements were taken prior to implantation of the repair device to assess the severity of the defect. Post repair measurements were taken 1 hour after repair and 3 hours after repair to assess the performance of the repair device. Mitral valve competence was assessed by analysis of the echocardiographic regurgitant vena contracta.

The experiment as described previously was conducted using six adult pigs (N=6). Each of the graphs 870, 890, and 910 show a baseline data set 872, 892, 912 and a post repair data set(s) 874, 894, 914. The baseline 872, 892, 912 data sets are generated by measuring the mitral valve regurgitation, left atrial pressure, peak mitral valve gradient a normal valve. The baseline measurements are taken to a valve similar to the defect-free valve 704 in FIG. 20. Graphs 870 and 890 also show a mitral regurgitation data set 876, 896 that is measured after creating the cleft, before implanting the repair device. The mitral regurgitation data set 876, 896 measurements are taken using a valve similar to the valve 700 on the anterior leaflet cleft column 706 in FIG. 20. The post repair data sets 874, 894, 914 include data taken 1 hour (1 hr) post repair 878, 898 and 3 hours (3 hrs) post repair 880, 900. The post repair data sets 874, 894, 914 measurements are taken using a valve similar to the valve 700 on the repair result column 714 in FIG. 20.

Graph 870 shows the mitral valve regurgitation grade (degree of mitral valve leak) vs. the baseline data set 872, the mitral valve regurgitation data set 876, the 1 hr post repair data set 874, and the 3 hr post repair data set 880 for each of the six test pigs. The grades on the y-axis range from a minimum of 0 (no leak), 1 (trivial), 2 (mild), 3 (moderate to maximum), and 4 (open or massive leak). In the baseline data set 872 the six mitral valves of the test pigs have no leak (grade 0). The cleft results in a grade 4 leak as shown in the mitral valve regurgitation data set 876. The repair device is then implanted to correct the cleft. The post repair data sets 874 show the leak reduced to trivial (grade 1) or no leak (grade 0) in four test pigs, one test pig to mild (grade 2), and one test pig to moderate (grade 3) after 1 hr post repair. The two test pigs withe mitral valve regurgitation grades at 2 and 3 were further reduced to trivial (grade 1) and mild (grade 2) respectively after 3 hrs post repair. This reduction in the leak grade was statistically significant ($p<0.05$).

Graph 890 shows the left atrial pressure (mmHg) vs. the baseline data set 892, the mitral valve regurgitation data set 896, the 1 hr post repair data set 894, and the 3 hr post repair data set 900 for each of the 6 test pigs. The data sets, 892, 896, 898, 900 show the change in left atrial pressure in mmHg during same time line point as graph 870. The left atrial pressure increased from the baseline measurements to the mitral valve regurgitation measurements. The mitral valve regurgitation data set 896 was measured during the grade 4 leak directly after the cleft was surgically induced or formed. After the repair device was implanted, the left atrial pressure significantly ($p<0.05$) reduced to normal levels in the 1 hr post repair data set 898 and remained the in the 3 hr post repair data set 900.

Graph 910 shows the mitral valve peak gradient (mmHg) vs the baseline data set 912 and the post repair data set 914. In this test only four of the six test pigs were evaluated (N=4). The mitral valve peak gradient helps to evaluate the mitral valve orifice for any stenosis after implanting the repair device. A repaired valve with no significant change in the peak gradient indicates that the repair device did not critically shrink the valve orifice. There was no significant change in the peak gradient across the valve between the normal valve at baseline 912 and after implantation (post repair 914).

In GII, complete repair was achieved with 4 pairs of branches. In this group, four test pigs showed absent or trivial mitral valve regurgitation, while one test pig had mild a grade of mitral valve regurgitation within 3 hrs of recovery. No mitral valve gradient or leaflet restriction was observed in GII.

Particular embodiments of the subject matter have been described. Other embodiments are within the scope of the following claims.

What is claimed:

1. A repair device for repairing a valve of a heart, the repair device comprising:
   a main stem having a distal end and a proximal end,
   a papillary anchor disposed on the proximal end of the main stem, wherein the papillary anchor is configured to attach to a papillary muscle of the heart,
   an annulus anchor disposed on the distal end of the main stem, the annulus anchor configured to attach to a wall of the heart,
   a first branch extending from the main stem in a first direction and configured to attach to a first leaflet of the valve of the heart, and
   a second branch extending from the main stem in a second direction different from the first direction and configured to attach to a second leaflet of the valve,
   wherein the first and second branches are flexible.

2. The repair device according to claim 1, wherein when the papillary muscle is relaxed, the device is configured to be in a relaxed configuration in which the first and second branches are untensioned.

3. The repair device according to claim 1, wherein when the papillary muscle is contracted, the device is configured to be in a flexed position in which the first and second branches are taut.

4. The repair device according to claim 3, configured to move away from the first and second leaflets when the repair device moves from a relaxed position to the flexed position.

5. The repair device according to claim 1, wherein the main stem extends along a longitudinal axis and the first and second branches extend from the main stem at an angle relative to the longitudinal axis.

6. The repair device according to claim 1, wherein the main stem has a circular or rectangular cross section.

7. The repair device according to claim 1, wherein the device comprises a plurality of first and second branches.

8. The repair device according to claim 1, wherein the first branch comprises multiple sub-branches, at least one of the sub-branches extending in a direction different from a direction which at least one other of the sub-branches extends.

9. The repair device according to claim 8, wherein at least one of the sub-branches extends in a direction parallel to the second direction.

10. The repair device according to claim 8, wherein the second branch comprises multiple sub-branches, at least one of the sub-branches extending in a direction different from a direction which at least one other of the sub-branches extends.

11. The repair device according to claim 10, wherein at least one of the sub-branches extends in a direction parallel to the first direction.

12. The repair device according to claim 1, wherein at least one of the first and second branches comprises a loop.

13. The repair device according to claim 1, wherein at least a portion of the main stem is formed by a series of adjacent loops.

14. The repair device according to claim 1, wherein the first branch is configured to attach to an edge of the first leaflet, and wherein the second branch is configured to attach to an edge of the second leaflet.

15. The repair device according to claim 1, wherein the papillary anchor is configured to be sutured to the papillary muscle.

16. The repair device according to claim 1, wherein the second branch is configured to be attached to an underside of the second leaflet.

17. The repair device according to claim 1, wherein the first and second directions are parallel.

18. The repair device according to claim 1, wherein the main stem made from tissue engineered material.

19. The repair device according to claim 18, wherein the tissue engineered material is configured to enable the length of the main stem to be changed.

20. The repair device according to claim 1, wherein the main stem comprises stretchable material to lengthen or shorten a length of the main stem.

21. The repair device according to claim 1, wherein the first branch has a different length than the second branch.

22. The repair device according to claim 1, wherein the main stem has a ribbon-like structure.

23. The repair device according to claim 1, wherein the main stem is a membrane or sheet of material.

24. The repair device according to claim 1, wherein the main stem comprises braided or woven material.

25. The repair device according to claim 1, wherein at least a portion of the first branch is formed by a series of adjacent loops.

26. The repair device according to claim 1, wherein at least a portion of the second branch is formed by a series of adjacent loops.

27. A repair device for repairing a valve of a heart, the repair device comprising:
   a main stem formed from tissue engineered material, the main stem having a distal end and a proximal end,
   a papillary anchor disposed on the proximal end of the main stem, wherein the papillary anchor is configured to attach to a papillary muscle of the heart,
   a first branch extending from the main stem in a first direction and configured to attach to a first leaflet of the valve of the heart, and
   a second branch extending from the main stem in a second direction different from the first direction and configured to attach to a second leaflet of the valve,
   wherein the first and second branches are flexible.

* * * * *